(12) United States Patent
Eberwine et al.

(10) Patent No.: US 8,367,402 B2
(45) Date of Patent: Feb. 5, 2013

(54) EXTRANUCLEAR RNA SPLICING IN NEURONAL DENDRITES

(75) Inventors: James Eberwine, Philadelphia, PA (US); Kevin Miyashiro, Philadelphia, PA (US); Jason Glanzer, Omaha, NE (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 271 days.

(21) Appl. No.: 12/628,860

(22) Filed: Dec. 1, 2009

(65) Prior Publication Data

US 2010/0159525 A1 Jun. 24, 2010

Related U.S. Application Data

(63) Continuation of application No. 11/543,882, filed on Oct. 5, 2006, now abandoned, which is a continuation of application No. PCT/US2005/011637, filed on Apr. 7, 2005.

(60) Provisional application No. 60/560,039, filed on Apr. 7, 2004.

(51) Int. Cl.
*C12N 15/74* (2006.01)
*C12N 5/02* (2006.01)

(52) U.S. Cl. ..................................... 435/320.1; 435/325

(58) Field of Classification Search ........................ None
See application file for complete search history.

(56) References Cited

U.S. PATENT DOCUMENTS

2004/0106566 A1 6/2004 Lin et al.

OTHER PUBLICATIONS

Aakalu et al., "Dynamic visualization of local protein synthesis in hippocampal neurons." 2001, Neuron 30: 489-502.
Bassell et al., "Sorting of beta-actin mRNA and protein to neurites and growth cones in culture." 1998, J. Neurosci. 18: 251-65.
Bodian, "A Suggestive Relationship of Nerve Cell RNA With Specific Synaptic Sites." 1965, Proc. Natl. Acad. Sci. U.S.A., 53: 418-425.
Crino et al., "Molecular characterization of the dendritic growth cone: regulated mRNA transport and local protein synthesis." 1996, Neuron 17: 1173-87.
Eberwine, et al., "Local translation of classes of mRNAs that are targeted to neuronal dendrites." 2001, PNAS 98(13):7080-5.
Fan et al., "Survival motor neuron (SMN) protein: role in neurite outgrowth and neuromuscular maturation during neuronal differentiation and development." 2002, Hum. Mol. Genet. 11: 1605-14.
Gardiol et al., "Dendritic and postsynaptic protein synthetic machinery." 1999, J. Neurosci. Res. 19: 168-79.
Huber et al., "Role for rapid dendritic protein synthesis in hippocampal mGluR-dependent long-term depression." 2000, Science 288: 1254-7.
Job et al., "Identification of sites for exponential translation in living dendrites." 2001, Proc. Natl. Acad. Sci. U.S.A. 98: 13037-42.
Jurica et al., "Pre-mRNA splicing: awash in a sea of proteins." 2003, Mol. Cell 12: 5-14.
Martin et al., "Synapse-specific, long-term facilitation of aplysia sensory to motor synapses: a function for local protein synthesis in memory storage." 1997, Cell, 91: 927-38.
Staley et al., "Mechanical devices of the spliceosome: motors, clocks, springs, and things." 1998, Cell 92: 315-26.
Strehblow et al., "Nucleocytoplasmic distribution of human RNA-editing enzyme ADAR1 is modulated by double-stranded RNA-binding domains, a leucine-rich export signal, and a putative dimerization domain." 2002, Mol. Biol. Cell, 13: 3822-35.
Torre et al., "Protein synthesis within dendrites: glycosylation of newly synthesized proteins in dendrites of hippocampal neurons in culture." 1996, J. Neurosci. 16: 5967-78.

*Primary Examiner* — Nancy T Vogel
*Assistant Examiner* — Catherine Hibbert
(74) *Attorney, Agent, or Firm* — Riverside Law LLP

(57) ABSTRACT

The present invention relates to methods of synaptic network remodeling by means of extranuclear RNA splicing. The present invention also provides methods of extranuclear RNA splicing, and methods of protein translation based on extranuclear RNA splicing.

13 Claims, 17 Drawing Sheets

| SEQUENCE | EXON DONOR | 5' INTRON | 3' INTRON | EXON ACCEPTOR | OVERLAP | NOTES |
|---|---|---|---|---|---|---|
| CDC-preRNA Transfection of Isolated Dendrites | | | | | | |
| 1 | TTAAGTGTTGTACAG | ATACGAGAGCTCTAG | CTTTGAGACACTAAC | GTGTCCCCAGGGAGC | 0 | D |
| 2 | TCTCATTATTTAATG | TGGTTGGAGGACACA | CATGGAGAAGGCTCT | GACCCCTGAGTTGCT | 0 | C |
| 3 | CTGTGCTCCAGGTTG | CCACTGGAGTGATTT | AGGAGAACATGGAGA | AGGCTCTGACCCCTG | 0 | |
| 4 | TGCCACTGGAGTGAT | TTCTACCCTCCAGGT | CATGGAGAAGGCTCT | GACCCCTGAGTTGCT | 0 | |
| 5 | AAGGTTTCAGCTTCT | CATTATTTAATGTGG | TCCTTTTGCAGGTCA | ACAAGGAGAACATGG | 0 | |
| 6 | CGAGAGCTCTAGTCT | GGTCCTAACATGAAG | TGCAGGTCAACAAGG | AGAACATGGAGAAGG | 0 | D |
| 7 | CATTATTTAATGTGG | TTGGAGGACACATTT | CTGCCTCTCCTCTTT | GCAGGTCAACAAGGA | 0 | |
| 8 | TTGCGTGTTGTACAG | ATACGAGAGCTCTAG | CTTTGAGACACTAAC | GTGTCCCCAGGGAGC | 0 | |
| 9 | CTGGAGTGATTTCTA | CCCTCCAGGTAAGGT | CTCTCTCTCTGCCTC | TCCTCTTTGCAGGTC | 0 | |
| 10 | TTTCTACCCTCCAGG | TAAGGTTTCAGCTTC | CTCTTTGCAGGTCAA | CAAGGAGAACATGGA | 0 | |
| 11 | TCTGGTCCTAACATG | CTGACCCCTCACTCC | AACATGGAGAAGGCT | CTGACCCCTGAGTTG | 0 | |
| 12 | CCACTGGAGTGATTT | CTACCCTCCAGGTAA | CTTTGCAGGTCAACA | AGGAGAACATGGAGA | 0 | |
| 13 | ACCTGCTGACTGCTG | TGCTCCAGGTTGCCA | CAAGGAGAACATGGA | GAAGGCTCTGACCCC | 0 | |
| 14 | ATGTGGTTGGAGGAC | CATTTTAAGTGTTGT | CTCCTCTTTGCAGGT | CAACAAGGAGAACAT | 0 | |
| 15 | AGGTTGCCACTGGAG | TGATTTCTACCCTCC | GCCTCTCCTCTTTGC | AGGTCAACAAGGAGA | 0 | |
| 16 | GTTTCAGCTTCTCAT | TATTTAATGTGGTTG | ATGGAGAAGGCTCTG | ACCCCTGAGTTGCTG | 0 | |
| 17 | CTCTAGTCTGGTCCT | AACATGAAGACTTGC | AACAAGGAGAACATG | GAGAAGGCTCTGACC | 0 | |
| 18 | CTGTGCTCCAGGTTG | CCACTGGAGTGATTT | CAAGGAGAACATGGA | GAAGGCTCTGACCCC | 0 | |
| 19 | CTCATTATTTAATGT | GGTTGGAGGACACAT | AGAAGGCTCTGACCC | CTGAGTTGCTGTCTA | 0 | |
| 20 | CTTCTCATTATTTAA | TGTGGTTGGAGGACA | GGAGAAGGCTCTGAC | CCCTGAGTTGCTGTC | 0 | |
| 21 | AGTAAGGTTTCAGCT | TCTCATTATTTAATG | GTTGTGTCTACTGAT | CGGGGTAGACTACAA | 1 | |
| 22 | GACTGCTGTGCTCCA | GGTTGCCACTGGAGT | CTCTTTGCAGGTCAA | CAAGGAGAACATGGA | 1 | |
| 23 | TGGAGTGATTTCTAC | CCTCCAGGTAAGGTT | GCAAATGATAACCTC | TCTCTCTGCCTCTCC | 1 | |
| 24 | TAGTCTGGTCCTAAC | ATGAAGACTTGCTCA | GAGAAGGCTCTGACC | CCTGAGTTGCTGTCT | 1 | |
| 25 | CATGAAGACTTGCTC | ACTCCTACTGCTTGT | GGAGAAGGCTCTGAC | CCCTGAGTTGCTGTC | 1 | |
| 26 | GGACACATTTTAAGT | GTTGTACAGATACGA | TCTCTCTGCCTCT | CCTCTTTGCAGGTCA | 1 | |
| 27 | GAGTGATTTCTACCC | TCCAGGTAAGGTTTC | GGAGAAGGCTCTGAC | CCCTGAGTTGCTGTC | 1 | |
| 28 | AGGACACATTTTAAG | TGTTGTACAGATACG | AGGCTCTGACCCCTG | AGTTGCTGTCTACTG | 1 | |
| 29 | TGCTGTGCTCCAGGT | TGCCACTGGAGTGAT | GACCCCTGAGTTGCT | GTCTACTGATCGGGT | 1 | |
| 30 | GAGTGATTTCTACCC | CCCTGTAAGGTTTCA | AGAAGGCTCTGACCC | CCCTGAGTTGCTGTC | 1 | |
| 31 | GTTGTACAGATACGA | GCTCTAGTCTGGTCC | AGGAGAACATGGAGA | AGGCTCTGACCCCTG | 2 | |
| 32 | AGTAAGGTTTCAGCT | TCTCATTATTTAATG | CAAATGATAACCTCT | CTCTCTGCCTCTCCT | 2 | |
| 33 | AGGTAAGGTTTCAGC | CTCTCCTCTTTGCAG | AACCTCTCTCTCTGC | CTCTCCTCTTTGCAG | 2 | |
| 34 | TGACTGCTGTGCTCC | CAGGTTGCCACTGGA | GAGAAGGCTCTGACC | CCTGAGTTGCTGTCT | 2 | |
| 35 | TTTCTACCCTCCAGG | TAAGGTTTCAGCTTC | AGAACATGGAGAAGG | CTCTGACCCCTGAGT | 3 | A |
| 36 | TGCTGTGCTCCAGGT | GCCACTGGAGTGATT | GTCTACTGATCGGGT | AGACTACAAAGACGA | 3 | |
| 37 | GATTTCTACCCCCCA | TGTAAGGTTTCAGCT | CCTTGATGAAGTCCA | TTCTTTGAGACACTA | 3 | |
| 38 | GGTTTCAGCTTCTCA | TTATTTAATGTGGTT | CCTCTTTGCAGGTCA | ACAAGGAGAACATGG | 3 | |
| 39 | CTCTAGTCTGGTCCT | AACATGAAGACTTGC | AAGGCTCTGACCCCT | GAGTTGCTGTCTACT | 3 | |
| 40 | GCTGACTGCTGTGCT | CCAGGTTGCCACTGG | GACCCCTGAGTTGCT | GTCTACTGATCGGGT | 4 | |
| 41 | GTGATTTCTACCCTC | CAGGTAAGGTTTCAG | CTCTCTCTGCCTC | TCCTCTTTGCAGGTC | 4 | |
| 42 | TGATTTCTACCCTCC | TGTAAGGTTTCAGCT | TCTCTCTGCCTCTCC | TCTTTGCAGGTCAAC | 4 | |
| 43 | TATTTAATGTGGTTG | GAGGACACATTTTAA | CTGACCCCTGAGTTG | CTGTCTACTGATCGG | 4 | |
| 44 | GTGATTTCTACCCTC | CAGGTAAGGTTTCAG | TCTCTGCCTCTCCTC | TTTGCAGGTCAACAA | 4 | A |
| 45 | CTGGTCCTAACATGA | AGACTTGCTCACTCC | GGGAGCAGCAAATGA | TAACCTCTCTCTCTG | 4 | D |
| 46 | ACCCTCCAGGTAAGG | TTTCAGCTTCTCATT | TGCAGGTCAACAAGG | AGAACATGGAGAAGG | 4 | A |
| 47 | TTTAATGTGAAGACT | TGCTCACTCCTACTG | CTGATCGGGTAGACT | ACAAAGACGATGACG | 5 | D |
| 48 | TGCTGTGCTCCAGGT | TGCCACTGGAGTGAT | CTCCTCTTTGCAGGT | CAACAAGGAGAACAT | 5 | A |
| 49 | TCTGGTCCTAACATG | AAGACTTGCGTGTTG | AACAAGGAGAACATG | GAGAAGGCTCTGACC | 6 | B |
| 50 | GTGCCAAGCTTGCTG | ACTGCTGTGCTCCAG | ACCCCTGAGTTGCTG | TCTACTGATCGGGTA | 6 | |
| 51 | CTTGCTGACTGCTGT | GCTCCAGGTTGCCAC | CCCCTGAGTTGCTGT | CTACTGATCGGGTAG | 6 | |
| 52 | TTGCTACTCCTACTG | CTTGTTATGACCCCA | AGTTGCTGTCTACTG | ATCGGGTAGACTACA | 6 | |
| 53 | TCTGGTCCTAACATG | AAGACTTGCTCACTC | AACAAGGAGAACATG | GAGAAGGCTCTGACC | 6 | B |
| 54 | TTTAATGTGAAGACT | TGCTCACTCCTACTG | CTGATCGGGTAGACT | ACAAAGACGATGACG | | |
| Luciferase-SV40 pre-RNA | | | | | | |
| 1 | AAAGTCCAAATTGTA | CCAAATTGTAAAATG | TACTGTTTTTCTTA | CTCCACACAGGCATA | 2 | |
| 2 | AAGTCCAAATTGTAA | AATGTAACTGTATTC | CAGTTATAATCATAA | CATACTGTTTTTTCT | 2 | |
| 3 | TTACGTCGCCAGTCA | AGTAACAACCGCGAA | TAACAGTTATAATCA | TAACATACTGTTTTT | 3 | |
| 4 | CTTACCGGAAAACTC | GACGCAAGAAAAATC | TGTTTTTTCTTACTC | CACACAGGCATAGAG | 4 | |
| 5 | GATGACGGAAAAAGA | GATCGTGGATTACGT | CTCCTCCAAAAAAGA | AGAGAAAGGTAGAAG | 7 | |
| Sequences derived from Synaptoneurosome Splicing of CDC pre-RNA | | | | | | |
| 1 | CTTGCTCACTCCTAC | TGCTTGTTATGACCC | CTACTGATCGGGTAG | ACTACAAAGACGATG | 0 | |
| 2 | TTTTAAGTGTTGTAC | AGATACGAGAGCTCT | TCTCTGCCTCTCCTC | GATAACCTCTCTCTC | 0 | |
| 3 | TTCAGCTTCTCATTA | TTTAATGTGGTTGGA | TCCTCTTTGCAGGTC | AACAAGGAGAACATG | 1 | |
| 4 | AGGTTTCAGCTTCTC | ATTATTTAATGTGGT | CCTCTCTCTCTGCCT | CTCCTCTTTGCAGGT | 3 | |
| 5 | CTGACTGCTGTGCTC | CAGGTTGCCACTGGA | CCCCACCACAGGCAG | CTCAGATACACTTGG | 3 | |
| 6 | CCTCCAGGTAAGGTT | TCAGCTTCTCATTAT | TGCTGTCTACTGATC | GGGTAGACTACAAAG | 0 | |
| 7 | AGGTTTCAGCTTCTC | ATTATTTAATGTGGT | AAATGATAACCTCTC | TCTCTGCCTCTCCTC | 0 | |
| 8 | GCTTGTTATGACCCC | ACCACAGGCAGCTCAG | ACATGGAGAAGGCTC | TGACCCCTGAGTTGC | 7 | |
| 9 | TTCAGCTTCTCATTA | TTTAATGTGGTTGGA | CATTCTTTGAGACAC | TAACGTGTCCCCAGG | 0 | |
| 10 | CTTGCTGACTGCTGT | GCTCCAGGTTGCCAC | CTCTGACCCCTGAGT | TGCTGTCTACTGATC | 6 | |

NOTES
A    AG/GU CONSENSUS
B    IDENTICAL SEQUENCE
C    FROM TRANSFECTION/IVT EXPERIMENT
D    FROM TRANSLATION EXPERIMENTS

FIG. 1

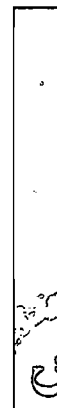
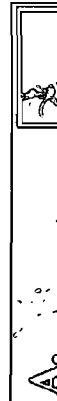
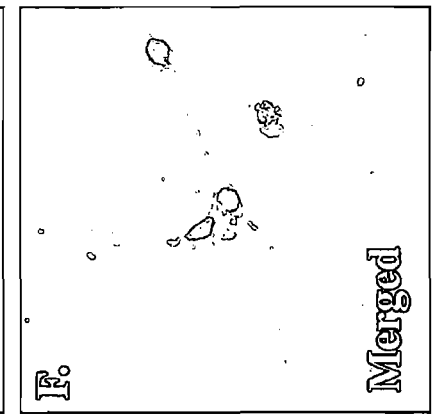
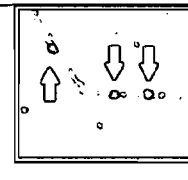
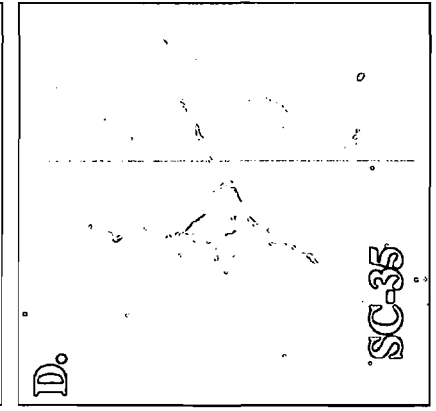

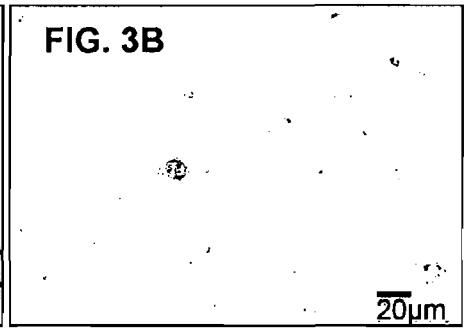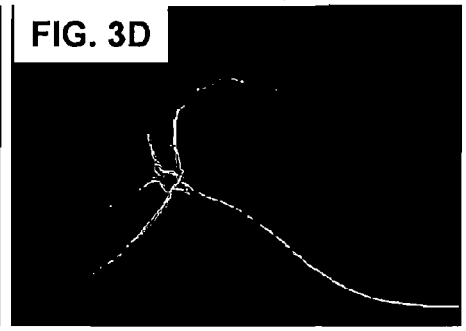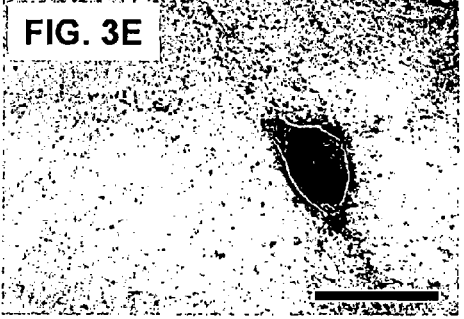

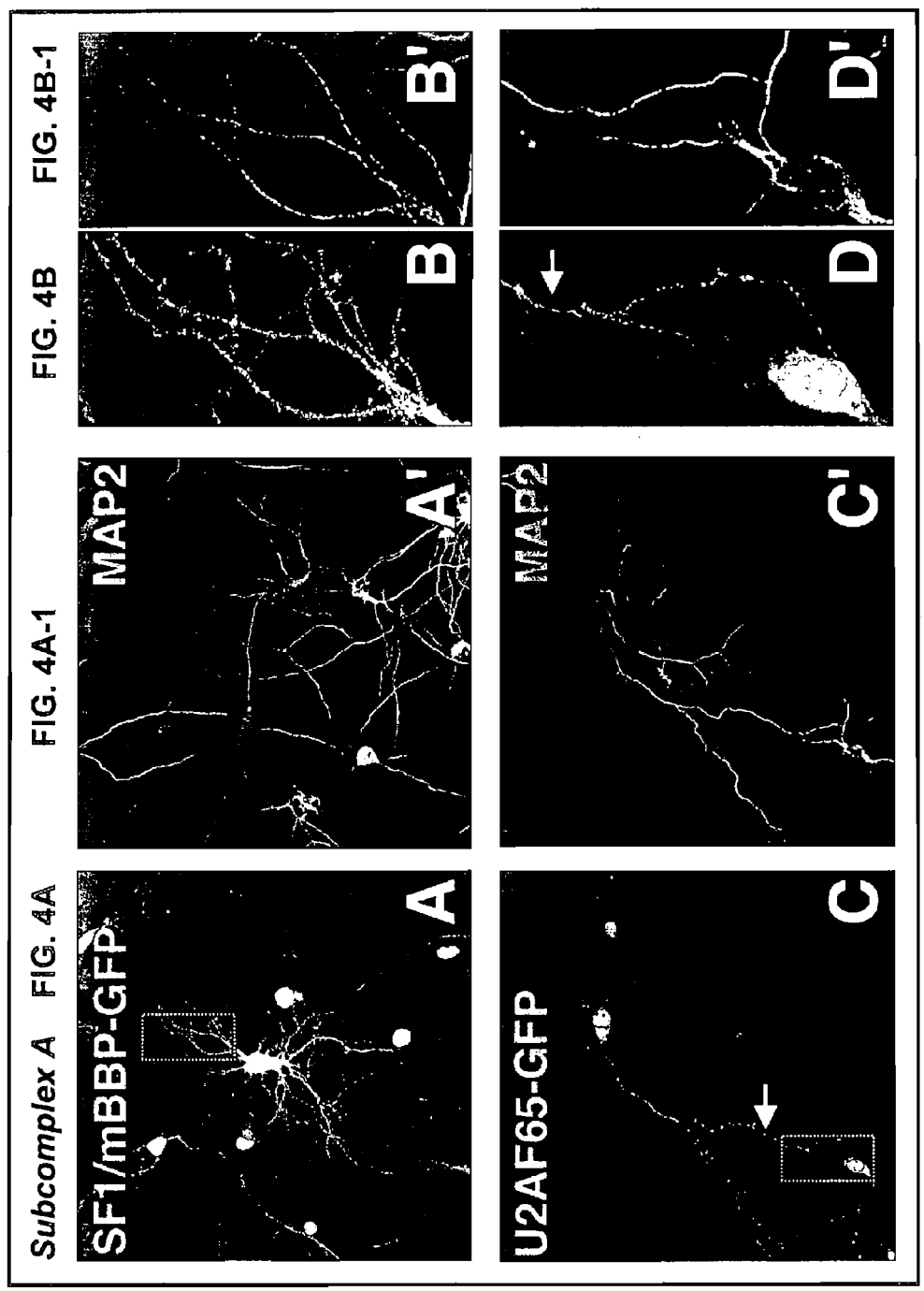

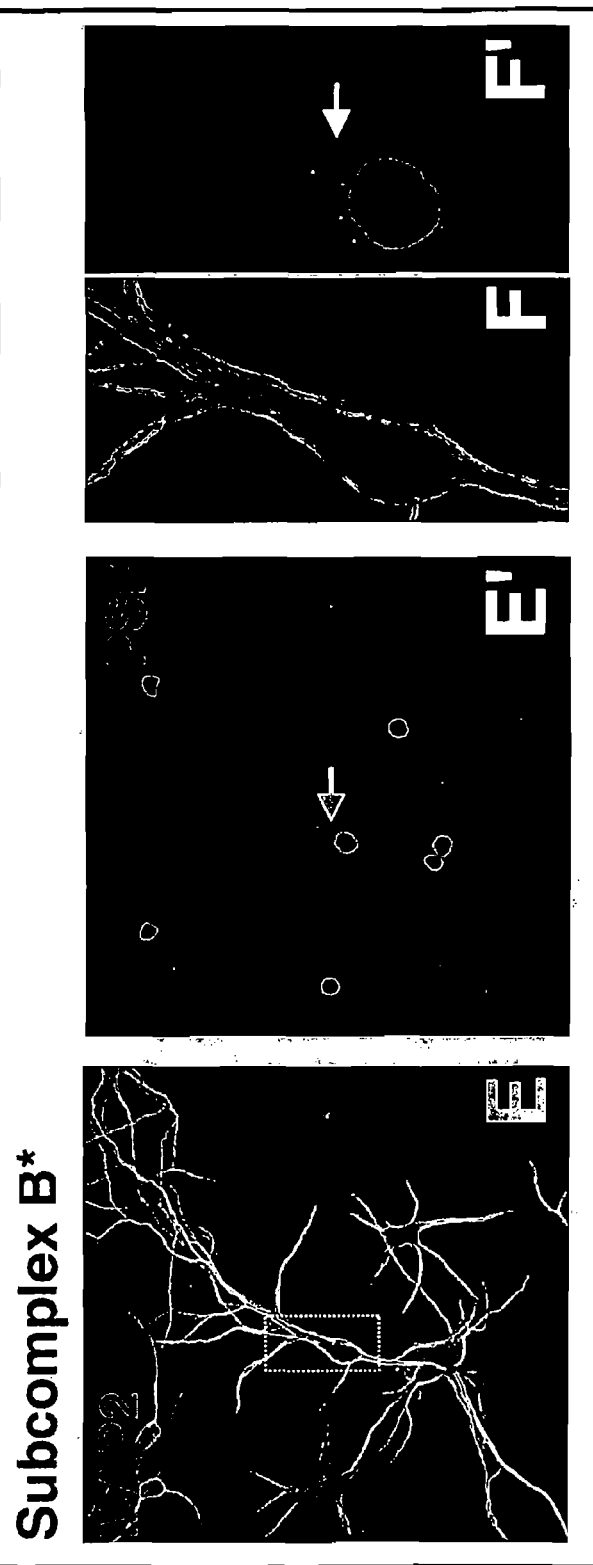

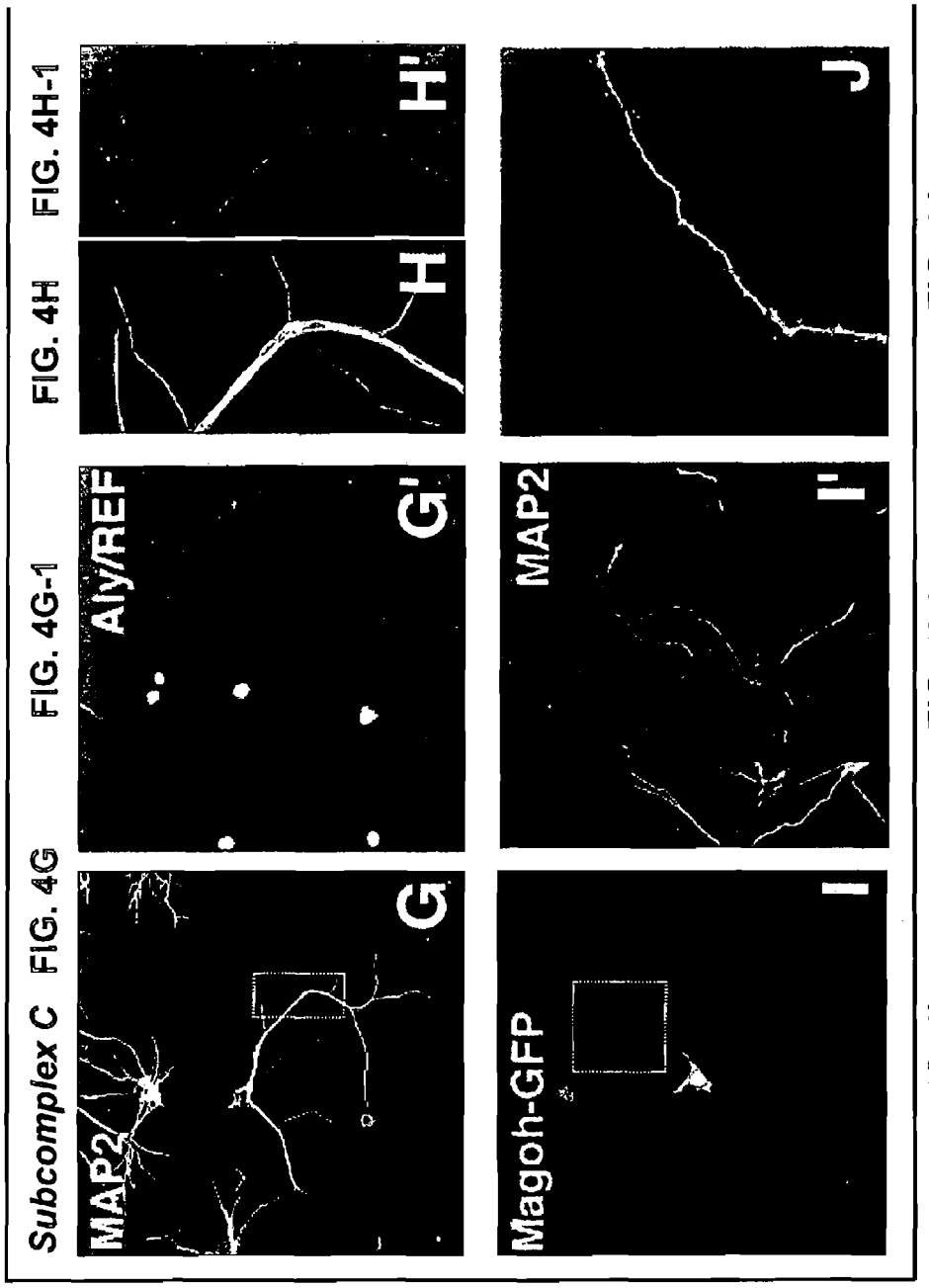

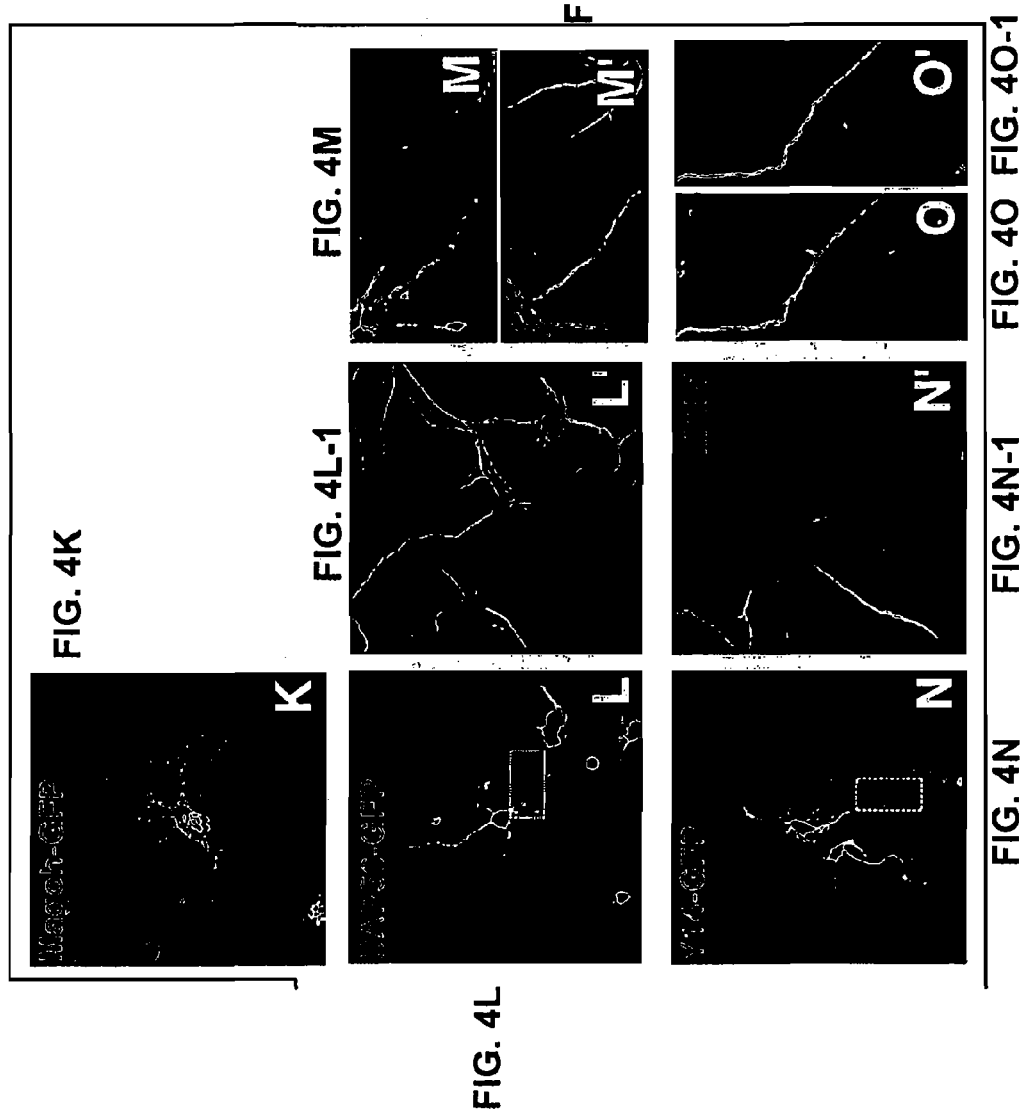

FIG. 7A          FIG. 7D
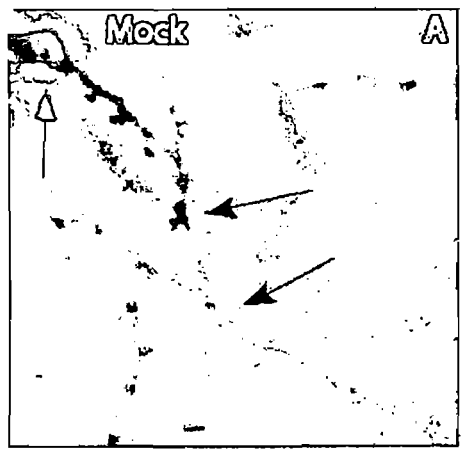 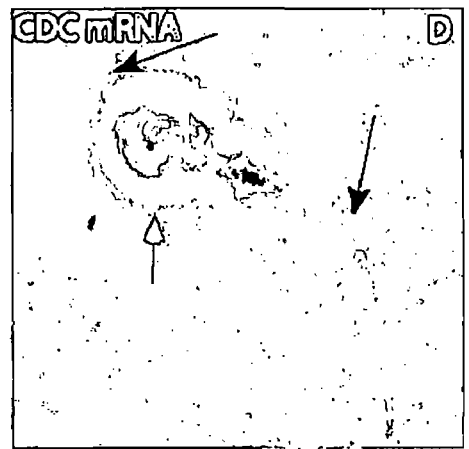
FIG. 7B          FIG. 7E
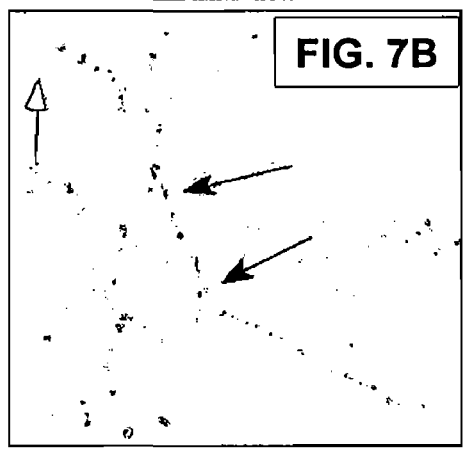 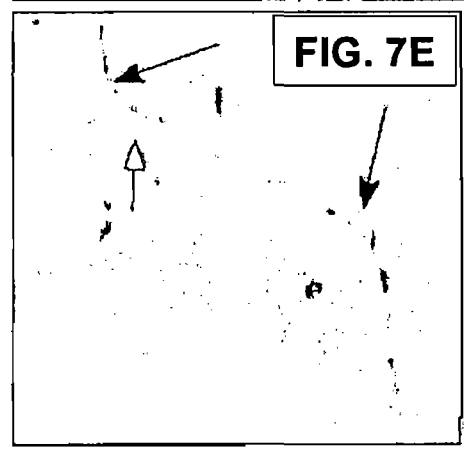
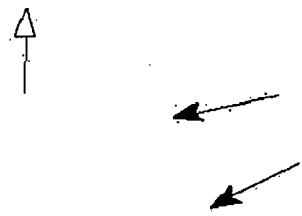 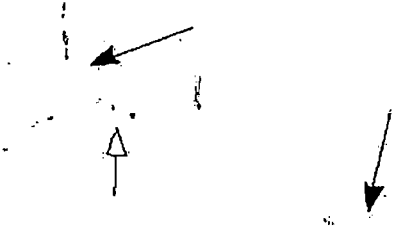
FIG. 7C          FIG. 7F

FIG. 8G
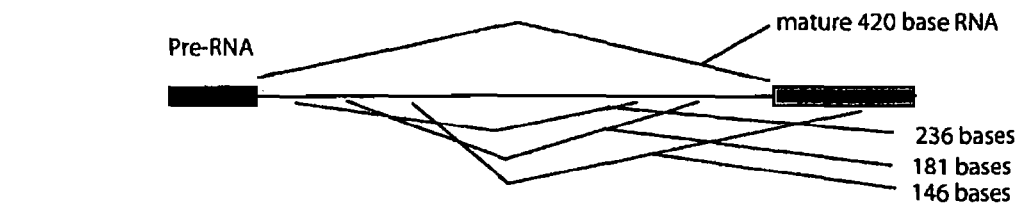
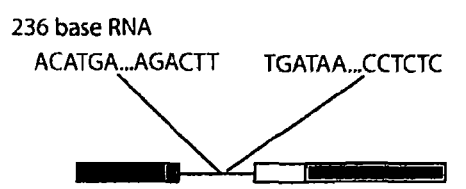
FIG. 8H
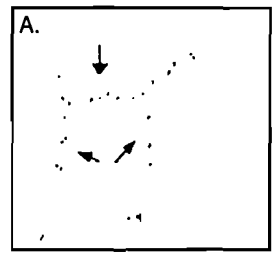
FIG. 8A
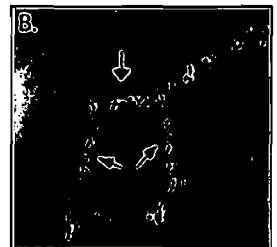
FIG. 8B
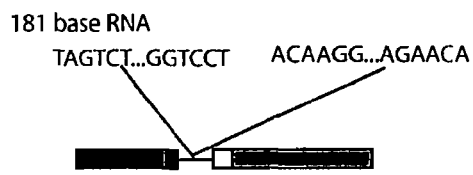
FIG. 8I
FIG. 8C
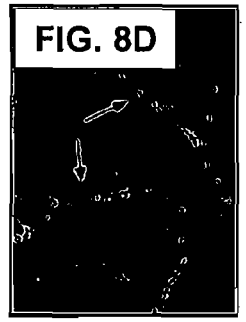
FIG. 8D
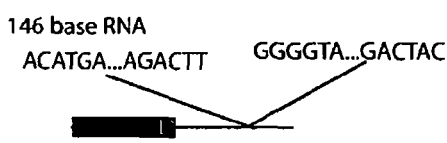
FIG. 8J
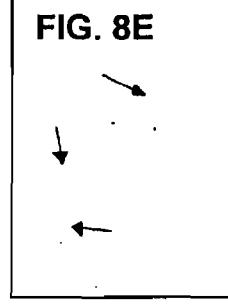
FIG. 8E
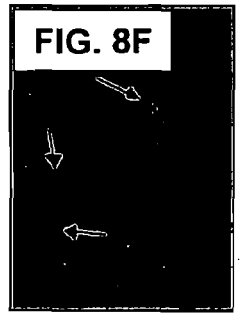
FIG. 8F

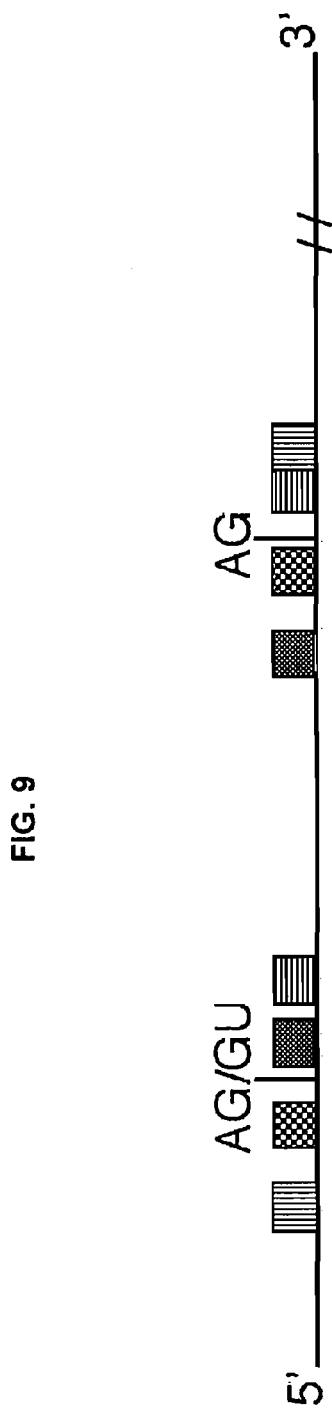

FIG. 10A
Neuronal Nuclei
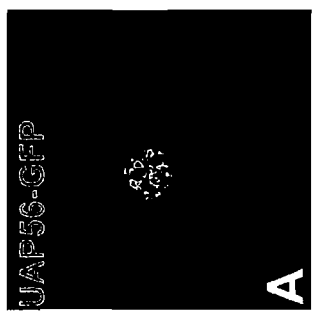
FIG. 10B
FIG. 10C
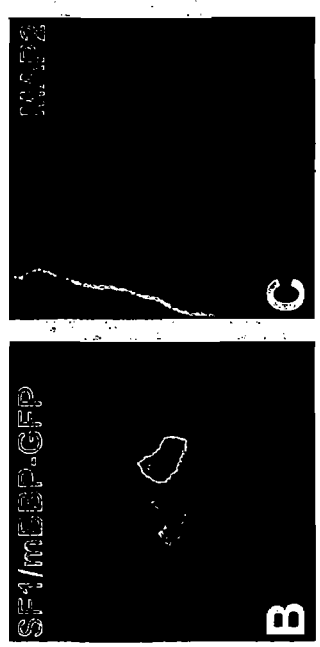
FIG. 10D
FIG. 10E
Non-neuronal RBP-GFP Expression

Control GFP Vector

Immuno-fluoresence Control

Transfection Control

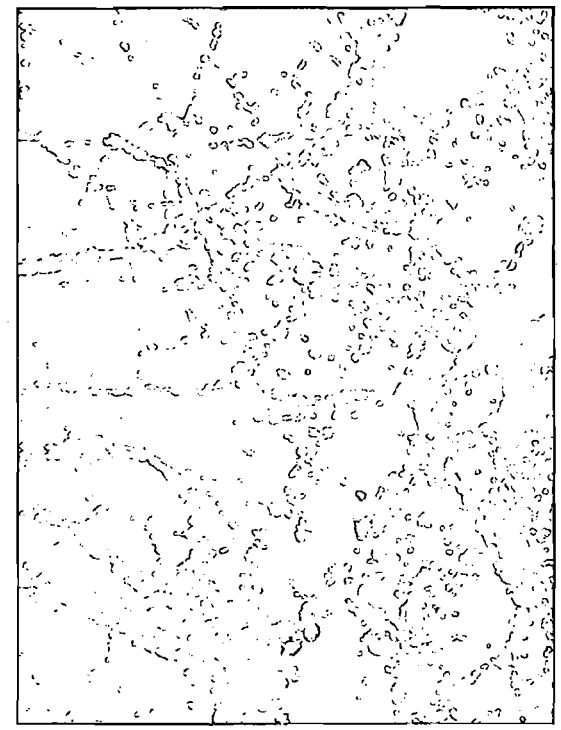
FIG. 11B  5 hr Post-Severing
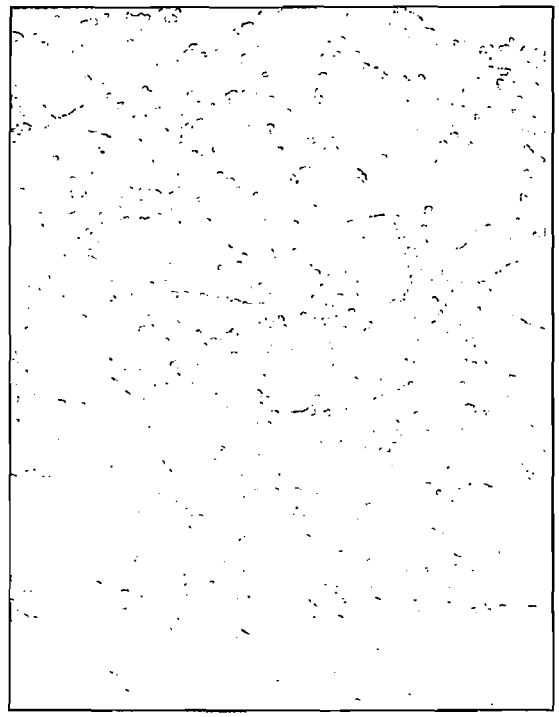
FIG. 11A  Immediately After Severing

EXTRANUCLEAR RNA SPLICING IN NEURONAL DENDRITES

This application is a continuation of U.S. application Ser. No. 11/543,882, filed Oct. 5, 2006 now abandoned, which in turn is a continuation of PCT International Application No. PCT/US2005/011637, filed Apr. 7, 2005, which in turn claims the benefit pursuant to 35 U.S.C. §119(e) of U.S. Provisional Application No. 60/560,039, filed on Apr. 7, 2004, all of which are hereby incorporated by reference in their entirety herein.

BACKGROUND OF THE INVENTION

In a living cell, such as a neuron, from the moment a primary RNA transcript is complete to the actual expression of the protein encoded by the transcript, multiple cellular events and mechanisms occur, including pre-RNA splicing, RNA editing, shuttling of the mRNA between the nucleus and the cytoplasm, and processes that ensure the stability and translational control of the trafficked mRNAs. Each of these events provides opportunities for the cell to regulate gene expression at the RNA level.

Each neuron is comprised of a nucleus within a body, or soma, a long fiber called the axon, and a varying number of branching fibers called dendrites, which extend out to other neurons. A single neuron can make numerous contacts with other neurons and tissues. For example, every new thought process is handled by a new set of synaptic connections. Memory itself is a set of synaptic connections engraved in the network of neurons.

Dendrites are specialized extensions of the neuronal soma that contain components of the cellular machinery involved in RNA and protein metabolism. A subset of mRNAs are trafficked to dendrites through their association with RNA binding proteins (RBPs). Some of these RBPs function in the nucleus as mediators of pre-RNA splicing.

The functional properties of neurites, including dendrites and axons, have been extensively examined since the discovery of protein synthetic machinery in dendrites, including ribosomes and membranous constituents of the endoplasmic reticulum and golgi apparatus (Bodian, 1965, Proc. Natl. Acad. Sci. U.S.A., 53:418-425; Steward et al., 1983, Res. 58:131-6; Torre et al., 1996, J. Neurosci. 16:5967-78; Gardiol et al., 1999, J. Neurosci. 19:168-79). Increasingly, more detailed molecular analyses of dendrites have shown that a subset of cellular RNAs are transported into dendrites where they can be translated into protein at specialized areas following synaptic stimulation (Aakalu et al., 2001, Neuron 30:489-502; Bassell et al., 1998, J. Neurosci. 18:251-65; Crino et al., 1996, Neuron 17:1173-87; Huber et al., 2000, Science 288: 1254-7; Job et al., 2001, Proc. Natl. Acad. Sci. U.S.A 98:13037-42; Martin et al., 1997, Cell, 91:927-38). In the cytoplasm, the intracellular transport, stability, and translation of RNA are regulated by RNA binding proteins (RBPs) (Spirin et al., 1979, Mol. Biol. Rep. 5:53-57). RBP-RNA interactions typically occur through conserved motifs in RBPs that associate with cis acting sequences or secondary structures in RNA.

Recently, other RBPs thought to function only in the nucleus have also been localized in the cytoplasm. These include RNA editing enzymes (e.g. double stranded RNA adenosine deaminase) (Strehblow et al., 2002, Mol. Biol. Cell, 13:3822-35) as well as some of the highly conserved constituents of the spiceosome (e.g. the survival of motor neuron proton (Fan et al., 2002, Hum. Mol. Genet. 11:1605-14) and a variety of heterogeneous nuclear ribonucleoproteins (hnRNPs) (Pinol-Roma, 1997, Semin. Cell Dev. Biol. 8:57-63). Some auxiliary components of the spliceosome, such as the splicing factor SAM68, are present within the somatodendritric compartment of neurons as well (Staley et al., 1998, Cell 92:315-26; Jurica et al., 2003, Mol. Cell 12:5-14; Grange et al., 2004, J. Neurosci. Res., 75:654-66). The presence of these proteins in a non-nuclear compartment suggests that they either serve a unique functional role outside of the nucleus or their known functional activity can occur within this subcellular compartment.

The spliceosome, which catalyses the ATP-dependent removal of introns from nuclear pre-RNA, is a multi-megadalton complex of proteins and small nuclear RNAs (snRNA) (Staley et al., 1998, Cell 92:315-26; Jurica et al., 2003, Mol. Cell 12:5-14). Even in the nucleus, the distribution of pre-RNA splicing factors is not uniform. Rather, within discrete sites of concentration and lower levels of factors diffusely dispersed throughout the nucleoplasm, speckles (splicing factor compartments) can be readily identified with an antibody against the spliceosome assembly factor SC-35 (Lamond et al., 2003, Nat. Rev. Mol. Cell Biol. 4:605-12).

Despite the existing knowledge of these nuclear factors in the cytoplasm, the current state of the art does not definitively attribute function or role to the presence of RBPs and spliceosome components in the cytoplasm. A greater understanding of the regulation, metabolism and growth of cells will enable more accurate and more useful control and manipulation of cells. The development of such tools can enable more precise, targeted therapies and treatments of all mammals, and in particular, of humans. Therefore, there exists a need for a better understanding of the function and role of RBPs and spliceosome components in the cytoplasm in order to facilitate the controlled manipulation of cells. The present invention addresses and meets these needs.

SUMMARY OF THE INVENTION

The present invention features a method of remodeling a dendrite comprising the steps of transfecting a dendrite with an RNA comprising at least one intron, wherein the dendrite comprises at least one component of a spliceosome and further wherein the component of a spliceosome is capable of splicing an RNA. The method also includes the step of allowing the RNA comprising at least one intron to be spliced by the spliceosome components and allowing the spliced RNA to be translated in the dendrite, wherein the dendrite is thereby remodeled as a consequence of the translation.

The invention also features a method of remodeling a dendrite interaction comprising the steps of transfecting a dendrite with an RNA comprising at least one intron, wherein the dendrite comprises at least one component of a spliceosome and further wherein the component of a spliceosome is capable of splicing an RNA. The method also includes the step of allowing the RNA comprising at least one intron to be spliced by the spliceosome components and allowing the spliced RNA to be translated in the dendrite, wherein the dendrite interaction is thereby remodeled as a consequence of the translation.

The present invention further features a method of remodeling a synaptic network comprising interaction with at least one dendrite comprising the steps of transfecting a dendrite with an RNA comprising at least one intron, wherein the dendrite comprises at least one component of a spliceosome and further wherein the component of a spliceosome is capable of splicing an RNA. The method also includes the step of allowing the RNA comprising at least one intron to be spliced by the spliceosome components and allowing the spliced RNA to be translated in the dendrite, wherein the synaptic network is thereby remodeled as a consequence of the translation.

In one aspect of the invention, a dendrite is a component of a neuron. In another aspect, a dendrite is an isolated dendrite.

The invention also provides a method of splicing an RNA comprising the steps of providing an isolated dendrite comprising at least one component of a spliceosome, wherein the component is capable of splicing an RNA, and transfecting the dendrite with an RNA comprising at least one intron, wherein the RNA comprising at least one intron is spliced by the spliceosome components.

The invention further provides a method of splicing an RNA comprising the steps of providing an isolated cell comprising at least one component of a spliceosome in the cytoplasm, wherein the component is capable of splicing an RNA, and transfecting a cell with an RNA comprising at least one intron, wherein the RNA comprising at least one intron is spliced by the spliceosome components in the cytoplasm.

In one aspect of the invention, the RNA splicing donor/acceptor pairs are selected from the group consisting of canonical, atypical and cryptic. In another aspect of the invention, an RNA comprising at least one intron is a pre-RNA. In another aspect, a pre-RNA is a pre-mRNA.

In one embodiment of the invention, an RNA comprising at least one intron is derived from a nucleic acid comprising a construct selected from the group consisting of pEGFP-N1, pDsRed-N1, SF1/mBBP-GFP, U2AF65-GFP, a GFP construct, a DsRed construct, a histone 2B-YFP construct.

In another embodiment of the invention, at least one spliceosome component is selected from the group consisting of Y14, Magoh, RNPS1, SC-35, SF2, U2AF65, Smith antigen, pan-SR antigen, U1 snRNP, U2 snRNP, U4 snRNP, U5 snRNP, U6 snRNP.

The invention also features a method of translating an RNA, comprising the steps of providing an isolated dendrite comprising at least one component of a spliceosome, wherein the component is capable of splicing an RNA, and transfecting the dendrite with an RNA comprising at least one intron, wherein the RNA is spliced by the spliceosome components.

The invention features a method of translating an RNA, comprising the steps of providing an isolated cell comprising at least one component of a spliceosome in the cytoplasm, wherein the component is capable of splicing an RNA, and transfecting the cell with an RNA comprising at least one intron, wherein the RNA is spliced by the spliceosome components in the cytoplasm. The method further includes translation of the spliced RNA.

The present invention also provides a method of splicing an RNA, comprising the steps of providing an isolated synaptoneurosome comprising at least one component of a spliceosome, wherein the component is capable of splicing an RNA, contacting said synaptoneurosome with an RNA comprising at least one intron, wherein the RNA comprising at least one intron is spliced by the spliceosome components.

The invention also features a method of translating an RNA, comprising the steps of providing an isolated synaptoneurosome comprising at least one component of a spliceosome, wherein the component is capable of splicing an RNA, contacting the synaptoneurosome with an RNA comprising at least one intron, wherein the RNA is spliced by the spliceosome components, and contacting the spliced RNA with a composition capable of translating an RNA under conditions suitable for translating an RNA.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1 is a chart depicting sequences of dendritically-spliced and synaptoneurosome-spliced RNAs. Sequences shown are, from the top left to the bottom right, SEQ ID Nos. 19-254. See also Table 1.

FIG. 2, comprising FIGS. 2A through 2L, is a series of images demonstrating coexistence of pre-spliceosome proteins in neuronal dendrites. FIGS. 2A through 2C are images of cultured hippocampal neurons labeled with Qdots 525/605 for detection of SC-35, U2AF and merged of FIGS. 2A and 2B, respectively. FIGS. 2D through 2F are images of cultured hippocampal neurons labeled with Qdots 525/605 for detection of SC-35, Sm antigen and merged of FIGS. 2D and 2E, respectively. FIGS. 2G through 2I are images of cultured hippocampal neurons labeled with Qdots 525/605 for detection of SC-35, SF2, and merged of FIGS. 2G and 2H, respectively. FIGS. 2J through 2L are images of cultured hippocampal neurons labeled with Qdots 525/605 for detection of SR, SF2, and merged of FIGS. 2J and 2K, respectively. MAP2 protein was detected in all samples via Cy5 immuno-detection and is shown in the inset panel in FIG. 2A. Qdot secondary antibodies alone without primary antibodies (see inset in FIGS. 2G and 2H) do not produce an observable signal in these cells.

FIG. 3, comprising FIGS. 3A through 3F, is a series of images demonstrating detection of U1 snRNA in dendrites. Neurons were subjected to in situ hybridization (ISH) with antisense digoxigenin-labeled U1 RNA (FIG. 3A) and a competition control where an excess of unlabelled U1 antisense RNA was hybridized to the section followed by washing and addition of digoxigenin-labeled RNA (FIG. 3B). Control ISH used digoxygeninlabeled GAD65 antisense RNA (FIG. 3E). Hybridized RNA was detected by alkaline phosphatase conjugated anti-digoxigenin antibody in the presence of NBT/BCIP. A strong nuclear presence of U1 RNA along with moderate staining within several dendrites was observed. Without wishing to be bound by any particular theory, background nuclear staining in FIG. 3B is attributed to hybridization to U1 genes and pseudogenes. FIGS. 3C and 3D show MAP2 immunofluorescence of antisense and competition control U1 in situ hybridizations, respectively, in order to identify the dendrites on these neurons. FIG. 3E depicts that GAD65 RNA is predominantly localized to the cell soma. There was little to no observable GAD65 ISH signal in the neuronal processes (as observed by phase contrast in FIG. 3F). The bright halo surrounding the neuron in phase-contrast (FIG. 3F) is a characteristic of healthy neurons whether live or fixed.

FIG. 4, comprising FIGS. 4A through 4O, is a series of images demonstrating distribution of selected components of spliceosomal subcomplexes A, B*, and C. Olympus Fluoview FV1000 images of primary hippocampal cells show the subcellular localization of the selected components of each spliceosome subcomplex. For subcomplex A, comprising FIGS. 4A through 4D, SF1/mBBP-GFP (FIG. 4A) and U2AF65-GFP (FIG. 4C) were used. Lower magnification whole cell views were stained for MAP2 with a Cy3 secondary antibody (FIGS. 4A-1 and 4C-1). A hatched box denotes the area highlighted by higher magnification views. Higher magnification of SF1/mBBP-GFP (FIGS. 4B and 4B-1) and U2AF65-GFP (FIGS. 4D and 4D-1) and their corresponding MAP2 immunofluorescence illustrate the presence of small puncta expressed throughout the dendrite. For subcomplex B*, immunofluorescence of anti-PSF monoclonal antibody in whole cell (FIG. 4E-1) and higher magnification view (FIG.

4F-1) are shown. Corresponding MAP2 immunofluorescence is shown using Alexa 488 secondary antibody for each of these views (FIGS. 4E and 4F). For subcomplex C, immunofluorescence of anti-Aly/REF monoclonal antibody with Cy3 secondary antibody in low (FIG. 4G-1) and high (FIG. 4H-1) magnification views is shown. Corresponding MAP2 immunofluorescence is shown using Alexa 488 (FIGS. 4G and 4H). GFP fusion constructs for Magoh, UAP56, or Y14 were used. Whole cell (FIGS. 4I, 4L, and 4N) or higher magnification of dendritic fields (FIGS. 4, 4J, 4M, and 4O) show the diffusely and more concentrated puncta within the dendroplasm. MAP2 immunofluorescence was visible in the red channel in both low (FIGS. 4I-1, 4L-1, and 4N-1) and high magnification (FIGS. 4M-1 and 4O-1). FIG. 4K depicts a whole cell view of a glial cell transfected with the Magoh-GFP construct. It was observed that Magoh-GFP expression and U2AF65-GFP show low levels of GFP expression with a readily visible nuclear distribution and diffused GFP fluorescence throughout the glial cytoplasm.

FIG. 5, comprising FIGS. 5A and 5B, demonstrates detection of CDC pre-RNA splicing in an Sm-antigen positive dendrite.

FIG. 8, comprising FIGS. 8A through 8J, is a series of images demonstrating that FLAG protein can be translated from alternatively spliced CDC RNAs. FIGS. 8G, 8H, 8I, and 8J depict schematics of CDC pre-RNA and processed CDC RNAs used in the isolated dendrite transfection assay. CDC RNAs were synthesized from alternatively spliced variants 1, 6, and 45 (see FIG. 1, also set forth in Table 1) and these RNAs were transfected into isolated dendrites and subjected to immunohistochemistry. FLAG immunoreactivity was visualized with DAB. Red, represents premature termination codon produced in first reading frame by alternative splicing. White, represents the initiator methionine of the second cistron. FIGS. 8A, 8C, and 8E are brightfield images of isolated dendrites transfected with 236 bp, 181 bp, and 146 bp RNAs, respectively and subsequent phase contrast images are depicted FIGS. 8B, 8D, and 8F, respectively. Black arrows indicate isolated dendrites and areas of varied FLAG immunoreactivity.

FIG. 9 is a schematic depicting clustering of CDC RNA splice junctions. FIG. 9 shows a linear representation of splice acceptor/donor cluster sites relative to the canonical splice pair AG/GU . . . AG. Acceptor/donor pairs are matched by their respective shading pattern.

FIG. 10, comprising FIGS. 10A through 10K, depicts control data for GFP fusion constructs. Control experiments we conducted using the Olympus Fluoview FV1000 to illustrate the specificity of the GFP fusion constructs.

FIG. 11, comprising FIGS. 11A and 11B, illustrates isolated dendrite viability evaluation using mitochondrial function measurement.

DETAILED DESCRIPTION OF THE INVENTION

Figures 2G, 2H, 2I:
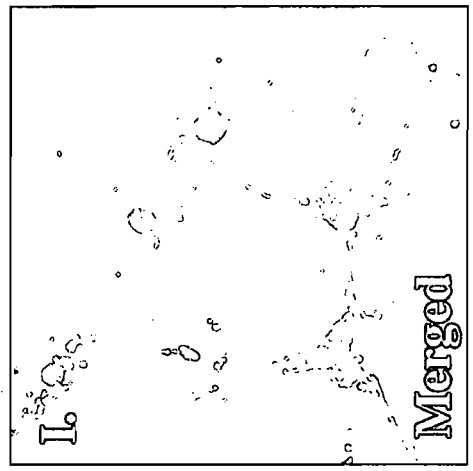
Figures 2J, 2K, 2L:
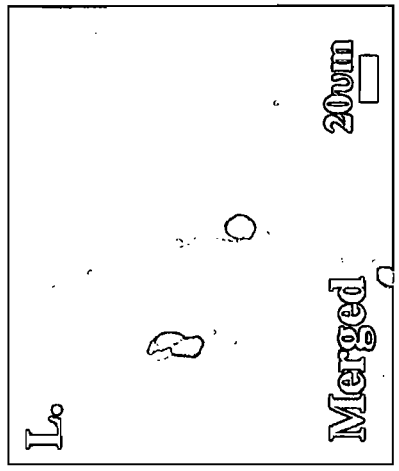

The morphology of a dendrite, and the manner of interaction of a dendrite with surrounding structures, including other neurons and neurites, including axons and other dendrites, plays a significant role in the electrophysiological characteristics of the dendrite. Dendritic interactions also play a role with respect to the "connectedness" of a neuron within a synaptic network.

In the present invention, the presence of nuclear RNA splicing machinery in dendrites is shown for the first time using multiple localization procedures. It is also shown for the first time herein that when isolated dendrites are transfected with a δ-crystallin(CDC) pre-RNA or luciferase reporter RNA containing an intron, splicing at canonical and cryptic splice acceptor/donor sites is obtained. Additionally, in vitro synaptoneurosome experiments set forth herein for the first time show that the cytoplasmic subcellular fraction contains a similar complement of splicing constituents that is able to splice CDC pre-RNA. Analysis of the CDC pre-mRNA spliced RNAs reveals that a subset of the dendritically-spliced transcripts can be locally translated.

Therefore, the present application features methods for dendritic-local splicing of RNA. This is because, as shown herein for the first time, RNA splicing can occur extranuclearly, and in particular, in the cytoplasm of a cell. The invention also features methods of remodeling the electrochemical and the physical structure of a dendrite using methods related to dendrite-local RNA splicing. Further, the invention features methods of remodeling the electrochemical and the physical structure of a dendrite using methods related to dendrite-local RNA splicing and subsequent dendrite-local protein translation.

The present invention also features methods of remodeling the electrochemical and the physical structure of a dendrite using methods related to dendrite-local RNA splicing any mammalian cell cytoplasm or non-nuclear cellular compartment or fraction, as well as methods of remodeling the electrochemical and the physical structure of a dendrite using methods related to dendrite-local RNA splicing and subsequent dendrite-local protein translation in any mammalian cell cytoplasm or non-nuclear cellular compartment or fraction.

It is also a feature of the present invention to provide methods for the cytoplasmic splicing of RNA in dendrites. Further, the invention provides methods cytoplasmic splicing and translation of RNA in any mammalian cell cytoplasm or non-nuclear cellular compartment or fraction.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The nomenclature used herein and the laboratory procedures used in analytical chemistry and organic syntheses described below are those well known and commonly employed in the art. Standard techniques or modifications thereof, are used for chemical syntheses and chemical analyses.

The articles "a" and "an" are used herein to refer to one or to more than one (i.e., to at least one) of the grammatical object of the article. By way of example, "an element" means one element or more than one element.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

As used herein, to "alleviate" a disease, disorder or condition means reducing the severity of one or more symptoms of the disease, disorder or condition.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, to "treat" means reducing the frequency with which symptoms of a disease, disorder, or adverse condition, and the like, are experienced by a patient.

As the term is used herein, "modulation" of a biological process refers to the alteration of the normal course of the biological process.

As used herein, the term "remodel" relates to an alteration of the state or condition of something from a previous state or condition. For example, a neural network is "remodeled" as a result of a procedure or treatment if at least one neural connection or interface is changed from a previous state or condition as a result of the procedure or treatment.

The term "dendrite contact," as used herein, indicates physical contact of a dendrite with another physiological structure, including, but not limited to a second dendrite, an axon, a neurite, or a soma. The term "dendrite interaction" or "interaction with a dendrite" indicates at least one of chemical and physical contact of a dendrite with another physiological structure, but does not require physical contact with a dendrite.

As used herein, the term "synaptic network" refers to an interconnected network of neurons, and may include other components. The term "neural network" also refers to a network of neurons, and may include other components.

DESCRIPTION OF THE INVENTION

A. Methods of Splicing and Translating RNA

The present invention features a method of splicing RNA in a dendrite. It has been shown for the first time herein that, using a dendrite, which is a specialized extension of a neuron involved in interconnecting other neurons, RNA can be spliced outside of the nucleus. It has also been shown for the first time herein that, using the splicing capability of dendrites, RNA can be spliced outside of the nucleus. RNA splicing is useful for various purposes in the field of genetics and molecular biology, including the production of stable and properly organized transcripts, as well as the production of correctly-spliced and functional translated gene products. RNA splicing as described in the present invention is also useful for the genetic treatment of diseases in which the proper transcript is unstable or reactive. Delivery of a stable, unspliced transcript to a cell or an organism can enable the subsequent splicing and translation of the desired transcript.

In one embodiment of the invention, a method of splicing an RNA includes transfecting a dendrite with an RNA comprising at least one intron, wherein the dendrite comprises at least one component of a spliceosome, and the component of a spliceosome is capable of splicing an RNA. The transfected RNA is spliced by the spliceosome component within the dendrite. In one aspect of the invention, the dendrite is an isolated dendrite. That is, the dendrite is isolated from the rest of a neuron.

In an aspect of the invention, an RNA splicing donor/acceptor pair is a canonical pair. In another aspect of the invention, an RNA splicing donor/acceptor pair is an atypical pair. In yet another aspect of the invention, an RNA splicing donor/acceptor pair is a cryptic pair.

In an embodiment of the invention, an RNA comprising at least one intron is a pre-RNA. In one aspect, the RNA is a pre-mRNA. As discussed elsewhere herein, a pre-RNA is any RNA that can be processed to give rise to a molecularly distinct RNA molecule. Examples of pre-RNAs include, but are not limited to, an RNA that can be spliced to produce an RNA splice product that is shorter in length. As will be understood by the skilled artisan, intron-containing RNA useful in the present invention can be prepared in any number of ways, and the method of preparation of RNA should not be considered limiting. By way of a non-limiting example, RNA useful in the present invention may be prepared by methods including isolation of native RNA from a cell, isolation of RNA from a recombinant system in which a recombinant DNA construct was used to transcribe RNA, or from an RNA virus or a recombinant RNA virus (eg., rhinovirus, hepatitis C).

In one embodiment of the invention, RNA comprising at least one intron is derived from a recombinant DNA construct. A construct useful in the present invention is designed to provide a transcribed RNA comprising at least one splice site. Constructs useful in the present invention include, but are not limited to, pEGFP-N1, pDsRed-N1, SF1/mBBP-GFP, U2AF65-GFP, a GFP construct, a DsRed construct, a histone 2B-YFP construct. In another embodiment of the invention, a construct can also be engineered to comprise at least one intron. In one aspect, a construct is engineered so that RNA splicing produces a detectable product. By way of a non-limiting example, a construct can be engineered such that splicing results in an output of fluorescence.

In an embodiment of the invention, at least one spliceosome component is present in a cytoplasm useful for splicing an RNA according to a method of the present invention. In one aspect, a spliceosome component is identified by a detection process, as described in detail in the Experimental Examples of the present application. In another aspect, a spliceosome component can be recombinantly engineered to exist in a cytoplasm useful for splicing an RNA according to a method of the present invention. Such recombinant techniques are well-known in the art, and will not be discussed in detail herein. For example, the invention encompasses expression vectors and methods for the introduction of exogenous DNA into cells with concomitant expression of the exogenous DNA in the cells such as those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

By way of a non-limiting example, spliceosome components useful in the present invention include, but are not limited to, Y14, Magoh, RNPS1, SC-35, SF2, U2AF65, Smith antigen, pan-SR antigen, U1 snRNP, U2 snRNP, U4 snRNP, U5 snRNP and U6 snRNP.

In another embodiment of the invention, a dendrite is a component of a neuron. That is, the dendrite is attached to a neuron comprising at least a soma. In one embodiment, the neuron is isolated. In another embodiment, the neuron is maintained in culture. In yet another aspect of the invention, a dendrite is a component of a neuron, wherein the neuron is in vivo, in a living organism. In one embodiment, the neuron is a part of a neural network. In another embodiment, the neuron is a transplanted neuron. In one aspect, the neuron is a transplanted neuron that is not a part of a neural network, but has the potential to be stimulated to integrate into an existing neural network.

This is because it has been shown herein for the first time that dendrites contain components of the RNA spliceosome and of the cellular translation machinery, and that RNA can be spliced and subsequently translated outside of the nucleus. In one embodiment, the present invention features a method of splicing an intron-containing RNA in the cytoplasm of a dendrite, followed by the translation of the spliced RNA to the corresponding protein.

In one embodiment, a method of translating a spliced RNA includes transfecting a dendrite with an RNA comprising at least one intron, wherein the dendrite comprises at least one component of a spliceosome, and the component of a spliceosome is capable of splicing an RNA. The transfected RNA is spliced by the spliceosome component within the dendrite, and the spliced RNA is translated by the components of the translation machinery located within the dendrite.

In another embodiment of the invention, a method of translating a spliced RNA involves an isolated synaptoneurosome. In an embodiment of the invention, a method of translating a spliced RNA includes contacting a synaptoneurosome with an RNA comprising at least one intron, wherein the synaptoneurosome comprises at least one component of a spliceosome, and the component of a spliceosome is capable of splicing an RNA. The transfected RNA is spliced by the spliceosome component within the synaptoneurosome, and the spliced RNA is translated by the components of the translation machinery located within the synaptoneurosome.

In an aspect of the invention, the dendrite in which an RNA is translated is an isolated dendrite. In another aspect of the invention, a dendrite in which an RNA is translated is a component of a neuron. In one embodiment, the neuron is isolated. In another embodiment, the neuron is maintained in culture. In yet another aspect of the invention, a dendrite in which an RNA is translated is a component of a neuron, wherein the neuron is in vivo, in a living organism. In one embodiment, the neuron is a part of a neural network. In another embodiment, the neuron is a transplanted neuron. In one aspect, the neuron is a transplanted neuron that is not a part of a neural network, but has the potential to be stimulated to integrate into an existing neural network.

This is further because, as described in detail elsewhere herein, an RNA can be spliced and translated extranuclearly, within a dendrite. Translation of a particular spliced transcript locally within a dendrite can be used to remodel the dendrite. That is, the administration of a specific intron-containing RNA to a dendrite can be used to direct the local production of a protein that can be used to effect a change in the structure, biology, or electrophysiochemistry of a dendrite. By way of a non-limiting example, an intron-containing RNA is transfected into a dendrite, whereby the transfected RNA is specifically spliced, and the spliced transcript is translated locally to produce a protein that is useful for altering the physical structure and arrangement of the dendrite, thereby altering the neural connections of the dendrite. Such proteins include, but are not limited to, cadherin, BDNF receptor, and neurexin.

Therefore, the present invention also features a method of remodeling a dendrite, wherein the method includes transfecting a dendrite with an RNA comprising at least one intron, wherein the dendrite comprises at least one component of a spliceosome, and the component of a spliceosome is capable of splicing an RNA. The transfected RNA is spliced by the spliceosome component within the dendrite, and the spliced RNA is translated by the components of the translation machinery located within the dendrite. The protein produced by the translation consequently effects remodeling of the dendrite. In one aspect of the invention, the dendrite remodeling includes a physical alteration or restructuring of the dendrite. In another aspect of the invention, the dendrite remodeling includes an alteration of the chemical nature of the dendrite. In yet another aspect of the invention, the dendrite remodeling includes an alteration of the electrophysiochemical nature of the dendrite. In still another aspect of the invention, the dendrite remodeling includes an alteration of more than one property of the dendrite, such as, but not limited to, a physical restructuring of the dendrite that subsequently results in an alteration of the biological properties of the dendrite.

RNAs encoding proteins useful for remodeling a dendrite or a synaptic network include, but are not limited to, RNAs encoding cadherin, neurexin, synaptophysin, tubulin, microtubule associated proteins, and actin. As will be understood by the skilled artisan, when armed with the present application, RNAs encoding any protein known to be involved in the growth, homeostasis or remodeling of a dendrite are useful in the present invention. As will be understood by the skilled artisan, such RNAs may be pre-RNAs, and may be spliced to form the final useful RNA molecule.

One of skill in the art will understand, when armed with the present disclosure, that a multitude of properties of a dendrite, and by association, of a neuron, can be affected by the methods of the present invention. While not wishing to be bound by any particular theory, one of skill in the art will understand that a method of the present invention is useful for the growth of a synaptic network, by way of dendrite stimulation and remodeling, to form new and additional neuronal connections through dendrite remodeling. As will be understood by the disclosure set forth herein, such neural network growth and/or remodeling is useful in vitro, in a neuronal cell culture, or in vivo, in a patient in need of neural network growth and/or remodeling. Conditions for which neural network remodeling is useful include, but are not limited to, neurodegenerative diseases, such as Parkinson's disease, Alzheimers disease, Huntington's disease, fragile X disease, Downs' syndrome, and neuropsychiatric illnesses such as depression, schizophrenia, and schizo-affective disorders.

Therefore, the present invention also features a method of remodeling a synaptic network, wherein the method includes transfecting a dendrite with an RNA comprising at least one intron, wherein the dendrite comprises at least one component of a spliceosome, and the component of a spliceosome is capable of splicing an RNA. The transfected RNA is spliced by the spliceosome component within the dendrite, and the spliced RNA is translated by the components of the translation machinery located within the dendrite. The protein produced by the translation consequently effects remodeling of the dendrite, which results in remodeling of a synaptic network. In particular, the synaptic network comprising interaction with the transfected dendrite will thereby be remodeled.

As set forth in greater detail elsewhere herein, dendrite remodeling, and therefore, remodeling of the synaptic network comprising interaction with the transfected dendrite, includes one or more of a physical alteration or restructuring of the dendrite, alteration of the chemical nature of the dendrite, alteration of the electrophysiochemical nature of the dendrite, and alteration of the biological properties of the dendrite.

While the present invention is described in relation to the extranuclear, cytoplasmic splicing and translation of an RNA in relation to a dendrite, the skilled artisan reading the present disclosure will understand that the present invention is equally applicable to any cell. That is, the skilled artisan will understand that the methods of the present invention are equally applicable to use in the cytoplasm of any mammalian cell, including, but not limited to, human, primate, mouse, rat, equine, sheep, goat, pig and dog, among others. Further, the skilled artisan will understand that the methods of the present invention are based upon the phenomenon of RNA splicing, and subsequent translation of the spliced RNA, which processes are essential components of all mammalian cells.

Based on the disclosure set forth herein, the skilled artisan will understand how to identify components of the spliceosome extranuclearly, in the cytoplasm, and further, will understand how to identify components of the translation machinery in the cytoplasm. Further still, the skilled artisan, when equipped with the disclosure of the present invention, will understand how to assay for extranuclear RNA splicing and for translation of the spliced RNA product. Based on the extensive disclosure set forth herein, the routineer will understand that the present disclosure guides the skilled artisan to assay for extranuclear RNA splicing and for translation of the spliced RNA product using techniques available in the art and within the realm of ordinary and routine experimentation.

Therefore, the present invention also includes a method of splicing an RNA, including transfecting a cell with an RNA comprising at least one intron, wherein the cell comprises at least one component of a spliceosome in the cytoplasm, and the component of a spliceosome is capable of splicing an RNA. The transfected RNA is spliced by the spliceosome component within the cytoplasm of the cell. In one aspect of the invention, the cell is an isolated cell. As will be understood based on the discussion set forth herein, the cell can be any mammalian cell comprising a cytoplasm.

Further, in an embodiment of the invention, a method of translating a spliced RNA includes transfecting a cell with an RNA comprising at least one intron, wherein the cell comprises at least one component of a spliceosome in the cytoplasm, and the component of a spliceosome is capable of splicing an RNA. The transfected RNA is spliced by the spliceosome component within the cytoplasm, and the spliced RNA is translated by the cell. In another embodiment, the spliced RNA is translated by the components of the translation machinery located within the cytoplasm. In one aspect of the invention, the cell in which a spliced RNA is translated is an isolated cell. In another aspect of the invention, a cell in which a spliced RNA is translated is a component of a cell culture. In yet another aspect, a cell in which a spliced RNA is translated is part of a living organism, including, but not limited to, a human.

B. Methods of Assaying for the Presence of Spliceosome Components in the Cytoplasm of a Cell The present invention further includes a method of identifying a functional complement of spliceosome components in a cell. In one embodiment, a method of identifying a functional complement of spliceosome components in a cell comprises the introduction of an RNA, comprising at least one intron, into a non-nuclear compartment of a cell or of a non-nuclear sub-cellular fraction. In one aspect, the method comprises the step of detection of any splice products resulting from the administration of an RNA. In another aspect, the method comprises the step of detection of any protein produced as a result of the production of splice products resulting from the administration of an RNA.

By way of a non-limiting example, a cryptic splice site in exon 7 of the E1aPDH gene binds with high affinity to SC35 of the spliceosome machinery (Gabut et al., 2005, MCB 25:3286-3294). A construct that contains this splice site can be used according to a method of the present invention to produce a splice product that can be detected in a non-nuclear compartment of a cell or in a non-nuclear sub-cellular fraction.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Materials and Methods

Immunohistochemical detection of splicing proteins in neurons: E18 rat hippocampal neurons were prepared as previously described. 8-10 days later, cultured neurons were washed in pre-warmed Hank's balanced salt solution supplemented with 850 mg/Liter sodium bicarbonate, 20 mM HEPES, pH 7.4, and 1 mM sodium pyruvate then 1×PBS/ 0.12M sucrose for one minute each. Cells were fixed in 4% paraformaldehyde (Electron Microscopy Sciences) in PBS/ 0.12M sucrose for 7 minutes and washed three times in PBS/ 0.12M sucrose and two times in PBS/5 mM MgC12 for 5 minutes each. Cells were then permeabilized with 0.3% Triton-X 100/PBS for 5 minutes, washed three times in PBS/5 mM MgC12 for 5 minutes each, and stored in blocking solution (10% goat serum (Sigma), 0.1% fish gelatin, 0.1% Tween 20, in PBS] for 2 hrs. Cells were incubated overnight at 4° C. with the following primary antibodies diluted in 1% blocking solution/PBST (0.1% Tween/PBS): anti-Sm proteins (5 µg/ml, Lab Vision Corporation), anti SF2 (10 µg/ml, Zymed Laboratories INC. (this antibody does not recognize SC-35 or SF2)), anti-SC-35 (1:500, Accurate Chemical and Scientific Corporation), anti-SR (10 ug/ml Zymed Laboratories INC) and anti-U2AF65 (10 ug/ml Zymed Laboratories INC). Cells were then washed 3 times in PBST 5 minutes each and incubated for 2 hours in goat anti-mouse Qdot 525 (1:50, Quantum Dots, QDot Corp.). Neurons were washed 3 times in PBST for 10 minutes each, then sequentially labeled with rabbit polyclonal anti-MAP2 antibody (1:4000, kindly provided by Craig Garner, Stanford University) and a second primary antibody in 1% blocking solution/PBST overnight at 4° C. then washed 3 times in PBS/Tween and incubated 2 hours in Cy5 secondary antibody (1:250) and Qdot 605 (Quantum Dot 1:50). Following incubation, cells were washed 3 times in PBST, mounted with vectashield, and coverslips sealed with nail polish. Antibody dilution series were done with each antibody to determine the optimal dilution to use for these studies and secondary antibodies, absent primary antibodies showed no specific binding (data not shown). Confocal imaging was performed using a Fluoview 1000 confocal microscope (Olympus) and a three-channel confocal microscope (Prairie Technologies, WI) attached to an Olympus BX50 fixed-stage upright microscope, with excitation at 458 nm and 633 nm for imaging quantum dot (525, 605) and Alexa 633, respectively. For selective emission collection, 515±15 nm and 585±20 nm band pass filters were used for quantum dot imaging. To prevent bleed through, each quantum dot was imaged to setup laser power and photomultiplier gain before imaging triple-labeled samples. To confirm a lack of bleed-through between channels and confirm specificity of reactivity, samples were imaged in parallel when primary antibody was omitted. In some experiments we collected the emission spectra and confirmed the identity of each label. Z-stacks of confocal images were acquired by incrementing each image by 0.2 µm. Images were processed using Metamorph software (Universal Imaging, West Chester, Pa.). Other immunofluorescent images were taken on a Zeiss Axiovert 200 microscope attached to an Orca-ER camera (Hamamatsu) and processed with Axiovision 3.1 software (Zeiss), an Olympus IX81 microscope using FluoView, or an Olympus IX71 microscope using an Olympus DP12 camera.

Generation of spliceosome-related RBP constructs: cDNAs encoding rat Magoh, RNPS1, SF1/mBBP, USAF65, UAP56, and Y14 were isolated from whole rat brain by reverse transcription polymerase chain reaction using Pfu Turbo (Stratagene). Primers were designed according to the previously reported mouse or human sequences in GenBank. Primers for reIF4A3 are 5'-AATGAATTCGCCACCATG- GCGGCTAACGCCACGATGGCG-3' (SEQ ID NO:1) (sense; underlined nucleotides depict EcoRI site) and 5'-ATTTGGATCCCGAATTAGGTCAGCCA- CATTCATGGG-3' (SEQ ID NO:2) (antisense; underlined nucleotides depict BamHI site). Primers for rMagoh are 5'-AATAAGCTTGCCACCATGGAGAGT- GACTTTTACCTGCGT-3' (SEQ ID NO:3) (sense; underlined nucleotides depict HinDIII site) and 5'-ATTGACCG- GTGGGATTGGTTTAATCTTGAAGTGTAA-3' (SEQ ID NO:4) (antisense; underlined nucleotides depict AgeI site). Primers for rRNPS1 are 5'-AATAAGCTTGCCACCATG-GATTTATCAGGAGTGAAAAAG-3' (SEQ ID NO:5) (sense; underlined nucleotidesdepict HindDIII site) and 5'-ATTGACCGGTGGGAGCAGCCGTGAACCAACAGT-3' (SEQ ID NO:6) (antisense; underlined nucleotides depict AgeI site). Primers for rSF1/mBBP are 5'-AATGCTAGCGC-CACCATGGCGACCGGAGCGAACGCCACG-3' (SEQ ID NO:7) (sense; underlined nucleotidesdepict NheI site) and 5'-ATTTGGATCCCAATGGGCGCGGAAAGTCCTCAC-3' (SEQ ID NO:8) (antisense; underlined nucleotides depict BamHI site). Primers for rU2AF65 are 5'-AATAAGCTTGC-CACCATGGACTTCTTCAACGCCCAGATG-3' (SEQ ID NO:9) (sense; underlined nucleotides depict HinDIII site) and 5'-ATTTGGATCCCAGAAGTCCCGACGGTGG-TACGA-3' (SEQ ID NO:10) (antisense; underlined nucleotides depict BamHI site). Primers for rUAP56 are 5'-AATAAGCTTGCCACCATGGCAGAGAAC-GATGTGGACAAT-3' (SEQ ID NO:11) (sense; underlined nucleotides depict HinDIII site) and 5'-ATTTGGATCCCGT-GTCTGTTCAATGTAGGAGGA (SEQ ID NO:12) (antisense; underlined nucleotides depict BamHI site). Primers for rY14 are 5'-AATAAGCTTGCCACCATGGCGGACGT-GCTGGATCTTCAC-3' (SEQ ID NO:13) (sense; underlined nucleotides depict HinDIII site) and 5'-ATTTGGATC-CCGACGGCGTCTCCGGTCTGGACTCCT-3' (SEQ ID NO:14) (antisense; underlined nucleotides depict BamHI site). The PCR products were digested with the appropriate restriction enzyme and inserted into pEGFP-N1 or pDsRed-N1 (Clontech). All sequences were verified by sequencing and contain the full coding region in-frame with either GFP or DsRed.

DNA/Ca2+-phosphate coprecipitation transfection of DNA constructs into primary neuronal cell cultures: Primary hippocampal neurons were cultured for 7-10 days in vitro and then transfected as described by Park et al. with minor modifications (Park et al., 2004, Neurosci. Lett. 361:220-4).

In situ hybridization of U1 RNA: Hippocampal neurons were fixed in 4% paraformamide (10 min), washed 3×5 min in 0.01% triton-X100 PBS (PBST), washed 7 min in 0.2% triton-x100, PBS, and washed 2×5 min in PBS. After 3 hours in prehybridization buffer, at 50° C., hybridization buffer (50% formamide, 5×SSC, 1× Denhart's, 8% Dextran Sulfate, 10 mM DTT, yeast tRNA (50 ug/ml)) with 5 ng probe/µl and 8% dextran sulfate was added at 50° C. overnight. These hybridization conditions are quite stringent. Cells were washed 2×5 min 2×SSC at 50° C., 2×10 min 0.22×SSC at RT, and 1×30 min PBS1 µg/ml RNase A. Cells were then washed 2×5 min in PBS, blocked in PBST+10% goat serum for 30 min. Digoxigenin-labeled riboprobe antisense to bases 20 to 70 of U1 rat snRNA or GAD65 mRNA were detected with alkaline-phosphatase conjugated anti-DIG antibodies and visualized with BCIP/NBT. Antisense and RNase A controls were also performed.

CDC pre-RNA preparation and RNA transfection of neurons and dendrites: Pre- or mature CDCRNAs (pcDNA3 plasmid construct containing insert of exons 14 and IS of the CDC gene either with or lacking intermittent intron sequence and flanked with FLAG epitope; these constructs were kindly provided by Gideon Dreyfuss) were transcribed using Ambion's T7 mMESSAGE mMACHINE® kit. Approximately 1 µg of RNA was mixed with 5 µg1 of GeneP-ORTER® (Gene Therapy Systems) and incubated for 10 minutes at room temperature then stored on ice until use. Isolated dendrites were prepared by mechanical severing of the process from the cell soma and RNA/lipid mixtures applied to dendrites as previously described. Following transfection, (RS)-3,S-dihydroxy- phenyiglycine (DHPG, Tocris) was added to a final concentration of 20 µM in order to stimulate translation and isolated dendrites were incubated at 37° C. for one hour. Dendrites were washed four times in physiological buffer and fixed in 4% paraformaldehyde/PBS for 20 minutes then washed in PBS.

PCR Analysis of dendritic CDC RNA splice products: After transfection of hippocampal neurons with CDC RNA, dendrites were picked individually and a reverse transcription reaction performed using primer 'sp6'. An initial PCR reaction was performed using primers sp6 and 5A, then analyzed by gel electrophoresis. Successful amplification of mRNA results in the presence of a major 476 by fragment, with spliced products. The area immediately below the 476 by band is excised and gel purified, then reamplified utilizing the 5A primer and nested primer FLAG, then analyzed by gel electrophoresis. Samples displaying a positive splicing activity produce DNA fragments ranging in size from 125 by to 476 bp. These fragments were gel purified, cloned and sequenced. Reverse Transcription reaction: AMV-RT (Cape Cod) 42° C. 30 min. DNA amplifications were performed with Accuprime PFX DNA polymerase (Invitrogen): 1×95° C. 2 min, 40×95° C. 15 sec, 47° C. 30 sec, 68° C. 30 sec, 1×68° C. 7:00 min. Gel extractions were performed with the Qiaquick gel extraction kit (Qiagen). Fragments were A-tailed with Amplitaq (Perkin-Elmer) 10 min 68° C., then ligated to pGEM-T-Easy (Promega). Primers: sp6-ATTTAG-GTGACACTATAGA (SEQ ID NO:15), FLAG-TTTATCGT-CATCGTCTTTG (SEQ ID NO:16), 5A-CCAATC-GATATACTTAGCC (SEQ ID NO:17), 5B-GCCAGTGCCAAGCTTGCTGAC (SEQ ID NO:18).

Synaptoneurosome preparation: Protocol is adapted from (Weiler et al., 1993, Proc. Natl. Acad. Sci. U.S.A. 90:7168-71; Rao et al., 1993, J. Neurochem. 61:835-44). Briefly, 6-8 week old male Sprague-Dawley rats were sacrificed by cervical dislocation followed by rapid decapitation. After removal of the cerebellum, the brain is homogenized with a large dounce homogenizer (Wheaton) in cold isolation medium containing: 320 mM Sucrose, 10 mM Tris-HCl, 1 mM EDTA. The homogenate is spun at 3,500 rpm for three minutes and the supernatant is colleted and re-spun at 10,000 rpm for ten minutes. After re-suspension of the resultant pellet in 2.5 mls cold isolation medium, the solution is further homogenized and mixed with 12% Ficoll (Sigma). 7% Ficoll and isolation medium are then slowly layered on top of the homogenate, and solutions are spun at 27K RPM for 35 minutes (Beckman L8-55M). Synaptoneurosome fractions are then collected between the 12% and 7% Ficoll layers and kept on ice. For Western blotting, synaptoneurosomes or whole brain tissue is immediately pelleted and lysed in the presence of protease inhibitors. Equal amounts of protein (as determined by BradfordAssay) are run on NuPAGE 10% Bis-Tris precut gels (Invitrogen), transferred to PVDF membrane BioRad), stained using the antibodies listed above and visualized using chemiluminescence (PerkinElmer). Beta-tubulin is used as a loading control.

Experimental Example 1

Identification and Characterization of Splicesome Components in Neuronal Dendrites The spliceosome, which catalyses the ATP dependent removal of introns from nuclear pre-RNA, is a multi-megadalton complex of proteins and small nuclear RNAs (snRNA) (Staley et al., 1998, Cell 92:315-26; Jurica et al., 2003, Mol.

Cell 12:5-14). Even in the nucleus, the distribution of pre-RNA splicing factors is not uniform. Rather, with discrete sites of concentration and lower levels of factors diffusely dispersed throughout the nucleoplasm, speckles (splicing factor compartments) can be readily identified with an antibody against the spliceosome assembly factor SC-35 (Lamond et al., 2003, Nat. Rev. Mol. Cell Biol. 4:605-12). Initially, confocal microscopy was used to determine the immunofluorescent localization of the non-nuclear splicing factor domains (FIGS. 2A, 2D, and 2G) in primary neuronal dendrites. Expression outside of the nucleus clearly was observed as a series of puncta in the perinuclear space and dendrites (Buchhalter et al., 1991, Brain Res. Bull. 26:333-8). It was subsequently determined that other splicing factors associated with the initiation and commitment steps of pre-RNA splicing were also detectable in the dendritic arbor. Because SC-35 nuclear sites show relatively limited amounts of uridine incorporation, speckles are believed to be storage sites for numerous splicing factors and serine/arginine (SR)-rich proteins (Moen et al., 1995, Hum. Mol. Genet. 4:1779-89). Using antisera directed against four core components of the pre-spliceosome (i.e. SF2, U2AF65, Smith antigen (Sm), and pan-SR antigens), it was determined that these proteins co-exist with dendritically localized SC-35. (Buchhalter et al., 1991, Brain Res. Bull. 26:333-8) Each of these proteins has previously been detected in speckles of somatic nuclei as well as other nuclear subdomains.

Intrinsic to the pre-spliceosome complex are the Sm proteins that combine with snRNAs to form the core constituents of the small nuclear ribonucleoprotein particles (snRNPs); U1, U2, and U4-U6 (Will et al., 2001, Curr. Opin. Cell Biol. 13:290-301). In turn, the U1 snRNP is recruited to the nascent pre-RNA via the interaction between SF2 and intronic RNA sequence. During several other transitions, U2AF65, SF1/mammalian branch point binding protein (SF1/mBBP), and SR-rich proteins are subsequently recruited to the branch point sequence embedded in pre-RNA introns wherein rearrangements lock the U2 snRNP onto the pre-mRNA thereby committing to nuclear pre-RNA splicing (Guth et al., 1999, Mol. Cell Biol. 19:8263-71). When localization of these splicing factors was examined, high expression of USAF65 was observed (FIG. 2B), Sm antigen (FIG. 2E), SF2 (FIGS. 2H and 2K), and SR proteins (FIG. 2D) in the nuclei of both neurons and glia. These data are consistent with previous experiments noting their nuclear distribution. However, in each experiment, small puncta, or granule-like structures, were observed, located in proximal and distal portions of dendrites and their branch points. These granule-like bodies (Mattaj et al., 1985, Cell 40:111-8) were also observed in the perinuclear space of both neurons and glia often juxtaposed with the nuclear envelope (data not shown). For some proteins such as SF2, more granule-like structures were observed in the perinuclear space with reduced levels of SF2 puncta localized in proximal and distal dendrites (Tacke et al., 1995, Embo. J. 14:3540-51). The merged confocal images shown in FIGS. 2C, 2F, 2I and 2L illustrate the co-localization of each of the antigens with speckles or with each other. The presence of the pre-spliceosome-related antigens in the dendritic domain of the neurons was confirmed by co-localization of microtubule-associated protein 2 (MAP2) immunofluorescence (inset FIG. 2A). MAP2 is a protein marker of the somatodendritic domain of neurons. A predominantly nuclear localization, in contrast, was observed when using an anti-histone 3 antibody (see FIGS. 10E and 10F).

Since the traditional pre-RNA splicing complex also employs an RNA component, in situ hybridization (ISH) was performed for U1 RNA on rat hippocampal cultures. U1 RNA is the RNA component of the U1 snRNP and is critical for initiating traditional RNA splicing. ISH revealed the presence of U1RNA in the nucleus and more disperse localization in the cytoplasm and dendrites of many neurons (FIG. 3A). U1 RNA was interspersed along the length of dendrites, with noticeable staining occurring greater than 30 µm from the nucleus. Areas of moderate U1 staining also appeared at dendritic branch points. Antisense competition controls, where an excess of U1 antisense RNA is added to the prehybridization solution, washed away and labeled U1 antisense RNA annealed, showed only slight staining within the nucleus, potentially due to hybridization within multiple copies of the U1 RNA genes in the genome (FIG. 3B). Additionally, sense controls showed little staining. Dendrites are identified by MAP2 immunostaining (FIGS. 3C and 3D). The appearance of high levels of U1 RNA staining in the nucleus was expected (Huang et al., 1992, Proc. Natl. Acad. Sci. U.S.A. 89:305-8). By way of comparison the presence of U1 RNA in dendrites is contrasted with the dominant somatic localization of GAD65 mRNA in primary hippocampal neurons (FIGS. 3E and 3F). These data showing U1 RNA expression coupled with the evidence for pre-spliceosome constituents dispersed throughout the dendritic cytoplasm indicate that the assembly of functional core splicing components and more complex splicing mRNPs which would be required for the processing of select, dendritically localized mRNAs.

Following the initial commitment to splicing, constitutive pre-mRNA processing is also accompanied by a series of dynamic changes in the protein composition of the spliceosome. Three individual subcomplexes of the spliceosome (i.e. A (previously referred to as the pre-spliceosome), B*, and C) have recently been purified and their components identified by mass spec analysis (Hartmuth et al., 2002, Proc. Natl. Acad. Sci. U.S.A. 99:16719-24; Jurica et al., 2002, Rna 8:426-39; Makarov et al., 2002, Science, 298:2205-8). Having already explored the distribution of pre-spliceosome components, subcomplexes B* and C were examined. Subcomplex B* temporally represents the mRNP remodeling just prior to the first transesterification reaction while the catalytic C subcomplex represents the splice-intermediate stage following this first chemical step. In particular, spliced mRNAs acquire a set of specific protein complexes that assemble near exon-exon junctions. Components of this exon junction complex (EJC), a majority of which are found in subcomplex C (Makarov et al., 2002, Science, 298:2205-8), include SRm160, RNPS1, UAP56, Aly/REF, Upf3, eIF4A3, Y14, and Magoh (Kataoka et al., 2000, Mol. Cell 6:673-82). Assembling 20-24 nucleotides upstream of spliced junctions, these proteins function in all manner of RNA metabolism including mRNA export (Le Hir et al., 2000, Genes Dev. 14:1098-108), coactivation of splicing (Blencowe et al., 1998, Genes Dev. 12:996-1009; Mayeda et al., 1999, Embo. J. 18:4560-70; Mayeda et al. 1999, Mol. Cell Biol. 19:1853-63), and non-sense-mediated mRNA decay (NMD) (Kim et al., 2001, Science 293:1832-6). Well-characterized, commercially-available antibodies, were used to determine the dendritic localization of each of the splicing factors examined herein. However, it was not always apparent that the antibodies were able to detect the native proteins with sufficient sensitivity using immunofluorescence. In part, this is likely due to the large macromolecular mRNP complexes to which they are intrinsic that may sterically hinder antibody access. To circumvent these difficulties and as a secondary confirmation of splicing enzyme localization, splicing RBPs were engineered, fused in-frame with GFP or DsRed at the carboxy terminus so that the fluorescent marker would be targeted to the subcellular sites where the splicing factors were localized.

The rat splicing factors were PCR cloned from rat brain cDNA and their identities sequence verified. These splicing enzyme sequences have been submitted to Genbank. For complex A-related factors, SFUmBBP-GFP were generated (FIGS. 4A and 4B), as were U2AF65-GFP fusion constructs (FIGS. 4C and 4D). The U2AF65-GFP construct was used as a secondary confirmation of immunofluroescence data of splicing factor localization performed in FIG. 1 (see also Table 1). For complex B*, a commercially available antibody to the polypyrmidine tract-binding protein associated splicing factor was used (PSF, FIGS. 4E-1 and 4F-1) (Kanai et al., 2004, Neuron 43:513-25). Finally, for complex C, an antibody to Aly/REF (FIGS. 4G-1 and 4H-1) and GFP or DsRed fusion constructs containing the open reading frame of Magoh (FIGS. 4I and 4J), UAP56 (FIGS. 4L and 4M), Y14 (FIGS. 4N and 4O), and RNPS1 were used. GFP or DsRed fusion constructs were transfected into primary hippocampal cultures at 10-12 days in vitro using a calcium phosphate protocol (Park et al., 2004, Neurosci. Lett. 361:220-4). For low-resolution, whole cell images, the intensity of the laser was increased to clearly show dendritic signal. In doing so, signal in nuclei is often saturated wherein specific nuclear subcompartment fluorescence is saturated. Photomontages of Z-stack images illustrate the images obtained during these experiments. SF1-mBBP-GFP and U2AF65-GFP showed consistent nuclear localization complemented by larger puncta as well as more dispersed granule-like structures throughout the perinuclear and dendritic cytoplasm in higher magnification images. Of note is the similarity in expression patterns obtained for U2AF65-GFP and the previous U2AF65 immunofluorescence obtained in FIG. 2. Complex B* component PSF showed an altogether separate pattern of localization. As previously described, speckled nuclei were distinctly visible. However, a low but significant cytoplasmic staining was visible in the perinuclear space (see arrows in FIG. 4F-1). Experiments with complex C cofactors showed some variation in expression depending upon the protein. Aly/REF immunofluorescence was restricted mostly to nuclei. However, a consistently low level of diffuse signal was visible interspersed throughout the dendritic arbor. In comparison, Magoh-GFP, Y14-GFP, UAP56-GFP, and RNPS1-GFP were scattered in granule-like structures in the dendroplasm and speckle-like domains in the nucleoplasm (see FIG. 10). Experiments performed with anti-Magoh or -Y14 antibodies were used to confirm the pattern of signal obtained with the Magoh- or Y14-GFP constructs. Magoh and Y14 are known to directly interact and have been shown to be important for oskar mRNA localization in Drosophila during oogensis. When co-expressed in primary neurons, Magoh-GFP and Y14-DsRed show nearly complete co-localization (FIG. 4K).

TABLE 1

Sequences of dendritically-spliced and synaptoneurosome-spliced RNAs.

| | EXON DONOR | 5' INTRON | 3' INTRON | EXON ACCEPTOR | OVERLAP/NOTES |
|---|---|---|---|---|---|
| CDC-preRNA Transfection of Isolated Dendrites | | | | | |
| 1 | TTAAGTGTTGTACAG (SEQ ID NO: 19) | ATACGAGAGCTCTAG (SEQ ID NO: 20) | CTTTGAGACACTAAC (SEQ ID NO: 21) | GTGTCCCCAGGGAGC (SEQ ID NO: 22) | 0/D |
| 2 | TCTCATTATTTAATG (SEQ ID NO: 23) | TGGTTGGAGGACACA (SEQ ID NO: 24) | CATGGAGAAGGCTCT (SEQ ID NO: 25) | GACCCCTGAGTTGCT (SEQ ID NO: 26) | 0/C |
| 3 | CTGTGCTCCAGGTTG (SEQ ID NO: 27) | CCACTGGAGTGATTT (SEQ ID NO: 28) | AGGAGAACATGGAGA (SEQ ID NO: 29) | AGGCTCTGACCCCTG (SEQ ID NO: 30) | 0 |
| 4 | TGCCACTGGAGTGAT (SEQ ID NO: 31) | TTCTACCCTCCAGGT (SEQ ID NO: 32) | CATGGAGAAGGCTCT (SEQ ID NO: 33) | GACCCCTGAGTTGCT (SEQ ID NO: 34) | 0 |
| 5 | AAGGTTTCAGCTTCT (SEQ ID NO: 35) | CATTATTTAATGTGG (SEQ ID NO: 36) | TCCTTTTGCAGGTCA (SEQ ID NO: 37) | ACAAGGAGAACATGG (SEQ ID NO: 38) | 0 |
| 6 | CGAGAGCTCTAGTCT (SEQ ID NO: 39) | GGTCCTAACATGAAG (SEQ ID NO: 40) | TGCAGGTCAACAAGG (SEQ ID NO: 41) | AGAACATGGAGAAGG (SEQ ID NO: 42) | 0/D |
| 7 | CATTATTTAATGTGG (SEQ ID NO: 43) | TTGGAGGACACATTT (SEQ ID NO: 44) | CTGCCTCTCCTCTTT (SEQ ID NO: 45) | GCAGGTCAACAAGGA (SEQ ID NO: 46) | 0 |
| 8 | TTGCGTGTTGTACAG (SEQ ID NO: 47) | ATACGAGAGCTCTAG (SEQ ID NO: 48) | CTTTGAGACACTAAC (SEQ ID NO: 49) | GTGTCCCCAGGGAGC (SEQ ID NO: 50) | 0 |
| 9 | CTGGAGTGATTTCTA (SEQ ID NO: 51) | CCCTCCAGGTAAGGT (SEQ ID NO: 52) | CTCTCTCTCTGCCTC (SEQ ID NO: 53) | TCCTCTTTGCAGGTC (SEQ ID NO: 54) | 0 |
| 10 | TTTCTACCCTCCAGG (SEQ ID NO: 55) | TAAGGTTTCAGCTTC (SEQ ID NO: 56) | CTCTTTGCAGGTCAA (SEQ ID NO: 57) | CAAGGAGAACATGGA (SEQ ID NO: 58) | 0 |
| 11 | TCTGGTCCTAACATG (SEQ ID NO: 59) | CTGACCCCTCACTCC (SEQ ID NO: 60) | AACATGGAGAAGGCT (SEQ ID NO: 61) | CTGACCCCTGAGTTG (SEQ ID NO: 62) | 0 |
| 12 | CCACTGGAGTGATTT (SEQ ID NO: 63) | CTACCCTCCAGGTAA (SEQ ID NO: 64) | CTTTGCAGGTCAACA (SEQ ID NO: 65) | AGGAGAACATGGAGA (SEQ ID NO: 66) | 0 |
| 13 | ACCTGCTGACTGCTG (SEQ ID NO: 67) | TGCTCCAGGTTGCCA (SEQ ID NO: 68) | CAAGGAGAACATGGA (SEQ ID NO: 69) | GAAGGCTCTGACCCC (SEQ ID NO: 70) | 0 |

TABLE 1-continued

Sequences of dendritically-spliced and synaptoneurosome-spliced RNAs.

| | EXON DONOR | 5' INTRON | 3' INTRON | EXON ACCEPTOR | OVERLAP/NOTES |
|---|---|---|---|---|---|
| 14 | ATGTGGTTGGAGGAC (SEQ ID NO: 71) | CATTTTAAGTGTTGT (SEQ ID NO: 72) | CTCCTCTTTGCAGGT (SEQ ID NO: 73) | CAACAAGGAGAACAT (SEQ ID NO: 74) | 0 |
| 15 | AGGTTGCCACTGGAG (SEQ ID NO: 75) | TGATTTCTACCCTCC (SEQ ID NO: 76) | GCCTCTCCTCTTTGC (SEQ ID NO: 77) | AGGTCAACAAGGAGA (SEQ ID NO: 78) | 0 |
| 16 | GTTTCAGCTTCTCAT (SEQ ID NO: 79) | TATTTAATGTGGTTG (SEQ ID NO: 80) | ATGGAGAAGGCTCTG (SEQ ID NO: 81) | ACCCCTGAGTTGCTG (SEQ ID NO: 82) | 0 |
| 17 | CTCTAGTCTGGTCCT (SEQ ID NO: 83) | AACATGAAGACTTGC (SEQ ID NO: 84) | AACAAGGAGAACATG (SEQ ID NO: 85) | GAGAAGGCTCTGACC (SEQ ID NO: 86) | 0 |
| 18 | CTGTGCTCCAGGTTG (SEQ ID NO: 87) | CCACTGGAGTGATTT (SEQ ID NO: 88) | CAAGGAGAACATGGA (SEQ ID NO: 89) | GAAGGCTCTGACCCC (SEQ ID NO: 90) | 0 |
| 19 | CTCATTATTTAATGT (SEQ ID NO: 91) | GGTTGGAGGACACAT (SEQ ID NO: 92) | AGAAGGCTCTGACCC (SEQ ID NO: 93) | CTGAGTTGCTGTCTA (SEQ ID NO: 94) | 0 |
| 20 | CTTCTCATTATTTAA (SEQ ID NO: 95) | TGTGGTTGGAGGACA (SEQ ID NO: 96) | GGAGAAGGCTCTGAC (SEQ ID NO: 97) | CCCTGAGTTGCTGTC (SEQ ID NO: 98) | 0 |
| 21 | AGTAAGGTTTCAGCT (SEQ ID NO: 99) | TCTCATTATTTAATGT (SEQ ID NO: 100) | GTTGTGTCTACTGAT (SEQ ID NO: 101) | CGGGGTAGACTACAA (SEQ ID NO: 102) | 1 |
| 22 | GACTGCTGTGCTCCA (SEQ ID NO: 103) | GGTTGCCACTGGAGT (SEQ ID NO: 104) | CTCTTTGCAGGTCAA (SEQ ID NO: 105) | CAAGGAGAACATGGA (SEQ ID NO: 106) | 1 |
| 23 | TGGAGTGATTTCTAC (SEQ ID NO: 107) | CCTCCAGGTAAGGTT (SEQ ID NO: 108) | GCAAATGATAACCTC (SEQ ID NO: 109) | TCTCTGCCTCTCC (SEQ ID NO: 110) | 1 |
| 24 | TAGTCTGGTCCTAAC (SEQ ID NO: 111) | ATGAAGACTTGCTCA (SEQ ID NO: 112) | GAGAAGGCTCTGACC (SEQ ID NO: 113) | CCTGAGTTGCTGTCT (SEQ ID NO: 114) | 1 |
| 25 | CATGAAGACTTGCTC (SEQ ID NO: 115) | ACTCCTACTGCTTGT (SEQ ID NO: 116) | GGAGAAGGCTCTGAC (SEQ ID NO: 117) | CCCTGAGTTGCTGTC (SEQ ID NO: 118) | 1 |
| 26 | GGACACATTTTAAGT (SEQ ID NO: 119) | GTTGTACAGATACGA (SEQ ID NO: 120) | TCTCTCTGCCTCT (SEQ ID NO: 121) | CCTCTTTGCAGGTCA (SEQ ID NO: 122) | 1 |
| 27 | GAGTGATTTCTACCC (SEQ ID NO: 123) | TCCAGGTAAGGTTTC (SEQ ID NO: 124) | GGAGAAGGCTCTGAC (SEQ ID NO: 125) | CCCTGAGTTGCTGTC (SEQ ID NO: 126) | 1 |
| 28 | AGGACACATTTTAAG (SEQ ID NO: 127) | TGTTGTACAGATACG (SEQ ID NO: 128) | AGGCTCTGACCCCTG (SEQ ID NO: 129) | AGTTGCTGTCTACTG (SEQ ID NO: 130) | 1 |
| 29 | TGCTGTGCTCCAGGT (SEQ ID NO: 131) | TGCCACTGGAGTGAT (SEQ ID NO: 132) | GACCCCTGAGTTGCT (SEQ ID NO: 133) | GTCTACTGATCGGGT (SEQ ID NO: 134) | 1 |
| 30 | GAGTGATTTCTACCC (SEQ ID NO: 135) | CCCTGTAAGGTTTCA (SEQ ID NO: 136) | AGAAGGCTCTGACCC (SEQ ID NO: 137) | CCCTGAGTTGCTGTC (SEQ ID NO: 138) | 1 |
| 31 | GTTGTACAGATACGA (SEQ ID NO: 139) | GCTCTAGTCTGGTCC (SEQ ID NO: 140) | AGGAGAACATGGAGA (SEQ ID NO: 141) | AGGCTCTGACCCCTG (SEQ ID NO: 142) | 2 |
| 32 | AGTAAGGTTTCAGCT (SEQ ID NO: 143) | TCTCATTATTTAATG (SEQ ID NO: 144) | CAAATGATAACCTCT (SEQ ID NO: 145) | CTCTCTGCCTCTCCT (SEQ ID NO: 146) | 2 |
| 33 | AGGTAAGGTTTCAGC (SEQ ID NO: 147) | CTCTCCTCTTTGCAG (SEQ ID NO: 148) | AACCTCTCTCTGC (SEQ ID NO: 149) | CTCTCCTCTTTGCAG (SEQ ID NO: 150) | 2 |
| 34 | TGACTGCTGTGCTCC (SEQ ID NO: 151) | CAGGTTGCCACTGGA (SEQ ID NO: 152) | GAGAAGGCTCTGACC (SEQ ID NO: 153) | CCTGAGTTGCTGTCT (SEQ ID NO: 154) | 2 |
| 35 | TTTCTACCCTCCAGG (SEQ ID NO: 155) | TAAGGTTTCAGCTTC (SEQ ID NO: 156) | AGAACATGGAGAAGG (SEQ ID NO: 157) | CTCTGACCCCTGAGT (SEQ ID NO: 158) | 3/A |
| 36 | TGCTGTGCTCCAGGT (SEQ ID NO: 159) | GCCACTGGAGTGATT (SEQ ID NO: 160) | GTCTACTGATCGGGT (SEQ ID NO: 161) | AGACTACAAAGACGA (SEQ ID NO: 162) | 3 |
| 37 | GATTTCTACCCCCCA (SEQ ID NO: 163) | TGTAAGGTTTCAGCT (SEQ ID NO: 164) | CCTTGATGAAGTCCA (SEQ ID NO: 165) | TTCTTTGAGACACTA (SEQ ID NO: 166) | 3 |
| 38 | GGTTTCAGCTTCTCA (SEQ ID NO: 167) | TTATTTAATGTGGTT (SEQ ID NO: 168) | CCTCTTTGCAGGTCA (SEQ ID NO: 169) | ACAAGGAGAACATGG (SEQ ID NO: 170) | 3 |

TABLE 1-continued

Sequences of dendritically-spliced and synaptoneurosome-spliced RNAs.

| | EXON DONOR | 5' INTRON | 3' INTRON | EXON ACCEPTOR | OVERLAP/NOTES |
|---|---|---|---|---|---|
| 39 | CTCTAGTCTGGTCCT (SEQ ID NO: 171) | AACATGAAGACTTGC (SEQ ID NO: 172) | AAGGCTCTGACCCCT (SEQ ID NO: 173) | GAGTTGCTGTCTACT (SEQ ID NO: 174) | 3 |
| 40 | GCTGACTGCTGTGCT (SEQ ID NO: 175) | CCAGGTTGCCACTGG (SEQ ID NO: 176) | GACCCCTGAGTTGCT (SEQ ID NO: 177) | GTCTACTGATCGGGT (SEQ ID NO: 178) | 4 |
| 41 | GTGATTTCTACCCTC (SEQ ID NO: 179) | CAGGTAAGGTTTCAG (SEQ ID NO: 180) | CTCTCTCTCTGCCTC (SEQ ID NO: 181) | TCCTCTTTGCAGGTC (SEQ ID NO: 182) | 4 |
| 42 | TGATTTCTACCCTCC (SEQ ID NO: 183) | TGTAAGGTTTCAGCT (SEQ ID NO: 184) | TCTCTCTGCCTCTCC (SEQ ID NO: 185) | TCTTTGCAGGTCAAC (SEQ ID NO: 186) | 4 |
| 43 | TATTTAATGTGGTTG (SEQ ID NO: 187) | GAGGACACATTTTAA (SEQ ID NO: 188) | CTGACCCCTGAGTTG (SEQ ID NO: 189) | CTGTCTACTGATCGG (SEQ ID NO: 190) | 4 |
| 44 | GTGATTTCTACCCTC (SEQ ID NO: 191) | CAGGTAAGGTTTCAG (SEQ ID NO: 192) | TCTCTGCCTCTCCTC (SEQ ID NO: 193) | TTTGCAGGTCAACAA (SEQ ID NO: 194) | 4/A |
| 45 | CTGGTCCTAACATGA (SEQ ID NO: 195) | AGACTTGCTCACTCC (SEQ ID NO: 196) | GGGAGCAGCAAATGA (SEQ ID NO: 197) | TAACCTCTCTCTCTG (SEQ ID NO: 198) | 4/D |
| 46 | ACCCTCCAGGTAAGG (SEQ ID NO: 199) | TTTCAGCTTCTCATT (SEQ ID NO: 200) | TGCAGGTCAACAAGG (SEQ ID NO: 201) | AGAACATGGAGAAGG (SEQ ID NO: 202) | 4/A |
| 47 | TTTAATGTGAAGACT (SEQ ID NO: 203) | TGCTCACTCCTACTG (SEQ ID NO: 204) | CTGATCGGGTAGACT (SEQ ID NO: 205) | ACAAAGACGATGACG (SEQ ID NO: 206) | 5/D |
| 48 | TGCTGTGCTCCAGGT (SEQ ID NO: 207) | TGCCACTGGAGTGAT (SEQ ID NO: 208) | CTCCTCTTTGCAGGT (SEQ ID NO: 209) | CAACAAGGAGAACAT (SEQ ID NO: 210) | 5/A |
| 49 | TCTGGTCCTAACATG (SEQ ID NO: 211) | AAGACTTGCGTGTTG (SEQ ID NO: 212) | AACAAGGAGAACATG (SEQ ID NO: 213) | GAGAAGGCTCTGACC (SEQ ID NO: 214) | 6/B |
| 50 | GTGCCAAGCTTGCTG (SEQ ID NO: 215) | ACTGCTGTGCTCCAG (SEQ ID NO: 216) | ACCCCTGAGTTGCTG (SEQ ID NO: 217) | TCTACTGATCGGGTA (SEQ ID NO: 218) | 6 |
| 51 | CTTGCTGACTGCTGT (SEQ ID NO: 219) | GCTCCAGGTTGCCAC (SEQ ID NO: 220) | CCCCTGAGTTGCTGT (SEQ ID NO: 221) | CTACTGATCGGGTAG (SEQ ID NO: 222) | 6 |
| 52 | TTGCTACTCCTACTG (SEQ ID NO: 223) | CTTGTTATGACCCCA (SEQ ID NO: 224) | AGTTGCTGTCTACTG (SEQ ID NO: 225) | ATCGGGTAGACTACA (SEQ ID NO: 226) | 6 |
| 53 | TCTGGTCCTAACATG (SEQ ID NO: 227) | AAGACTTGCTCACTC (SEQ ID NO: 228) | AACAAGGAGAACATG (SEQ ID NO: 229) | GAGAAGGCTCTGACC (SEQ ID NO: 230) | 6/B |
| 54 | TTTAATGTGAAGACT (SEQ ID NO: 231) | TGCTCACTCCTACTG (SEQ ID NO: 232) | CTGATCGGGTAGACT (SEQ ID NO: 233) | ACAAAGACGATGACG (SEQ ID NO: 234) | |

Luciferase-SV40 pre-RNA

| | EXON DONOR | 5' INTRON | 3' INTRON | EXON ACCEPTOR | OVERLAP/NOTES |
|---|---|---|---|---|---|
| 1 | AAAGTCCAAATTGTA (SEQ ID NO: 235) | CCAAATTGTAAAATG (SEQ ID NO: 236) | TACTGTTTTTTCTTA (SEQ ID NO: 237) | CTCCACACAGGCATA (SEQ ID NO: 238) | 2 |
| 2 | AAGTCCAAATTGTAA (SEQ ID NO: 239) | AATGTAACTGTATTC (SEQ ID NO: 240) | CAGTTATAATCATAA (SEQ ID NO: 241) | CATACTGTTTTTTCT (SEQ ID NO: 242) | 2 |
| 3 | TTACGTCGCCAGTCA (SEQ ID NO: 243) | AGTAACAACCGCGAA (SEQ ID NO: 244) | TAACAGTTATAATCA (SEQ ID NO: 245) | TAACATACTGTTTTT (SEQ ID NO: 246) | 3 |
| 4 | CTTACCGGAAAACTC (SEQ ID NO: 247) | GACGCAAGAAAAATC (SEQ ID NO: 248) | TGTTTTTTCTTACTC (SEQ ID NO: 249) | CACACAGGCATAGAG (SEQ ID NO: 250) | 4 |
| 5 | GATGACGGAAAAAGA (SEQ ID NO: 251) | GATCGTGGATTACGT (SEQ ID NO: 252) | CTCCTCCAAAAAAGA (SEQ ID NO: 253) | AGAGAAAGGTAGAAG (SEQ ID NO: 254) | 7 |

Sequences derived from Synaptoneurosome Splicing of CDC pre-RNA

| | EXON DONOR | 5' INTRON | 3' INTRON | EXON ACCEPTOR | OVERLAP/NOTES |
|---|---|---|---|---|---|
| 1 | CTTGCTCACTCCTAC (SEQ ID NO: 255) | TGCTTGTTATGACCC (SEQ ID NO: 256) | CTACTGATCGGGTAG (SEQ ID NO: 257) | ACTACAAAGACGATG (SEQ ID NO: 258) | 0 |
| 2 | TTTTAAGTGTTGTAC (SEQ ID NO: 259) | AGATACGAGAGCTCT (SEQ ID NO: 260) | TCTCTGCCTCTCCTC (SEQ ID NO: 261) | GATAACCTCTCTCTC (SEQ ID NO: 262) | 0 |
| 3 | TTCAGCTTCTCATTA (SEQ ID NO: 263) | TTTAATGTGGTTGGA (SEQ ID NO: 264) | TCCTCTTTGCAGGTC (SEQ ID NO: 265) | AACAAGGAGAACATG (SEQ ID NO: 266) | 1 |

TABLE 1-continued

Sequences of dendritically-spliced and synaptoneurosome-spliced RNAs.

| | EXON DONOR | 5' INTRON | 3' INTRON | EXON ACCEPTOR | OVERLAP/NOTES |
|---|---|---|---|---|---|
| 4 | AGGTTTCAGCTTCTC (SEQ ID NO: 267) | ATTATTTAATGTGGT (SEQ ID NO: 268) | CCTCTCTCTCTGCCT (SEQ ID NO: 269) | CTCCTCTTTGCAGGT (SEQ ID NO: 270) | 3 |
| 5 | CTGACTGCTGTGCTC (SEQ ID NO: 271) | CAGGTTGCCACTGGA (SEQ ID NO: 272) | CCCCACCACAGGCAG (SEQ ID NO: 273) | CTCAGATACACTTGG (SEQ ID NO: 274) | 3 |
| 6 | CCTCCAGGTAAGGTT (SEQ ID NO: 275) | TCAGCTTCTCATTAT (SEQ ID NO: 276) | TGCTGTCTACTGATC (SEQ ID NO: 277) | GGGTAGACTACAAAG (SEQ ID NO: 278) | 0 |
| 7 | AGGTTTCAGCTTCTC (SEQ ID NO: 279) | ATTATTTAATGTGGT (SEQ ID NO: 280) | AAATGATAACCTCTC (SEQ ID NO: 281) | TCTCTGCCTCTCCTC (SEQ ID NO: 282) | 0 |
| 8 | GCTTGTTATGACCCC (SEQ ID NO: 283) | ACCACAGGCAGCTCAG (SEQ ID NO: 284) | ACATGGAGAAGGCTC (SEQ ID NO: 285) | TGACCCCTGAGTTGC (SEQ ID NO: 286) | 7 |
| 9 | TTCAGCTTCTCATTA (SEQ ID NO: 287) | TTTAATGTGGTTGGA (SEQ ID NO: 288) | CATTCTTTGAGACAC (SEQ ID NO: 289) | TAACGTGTCCCCAGG (SEQ ID NO: 290) | 0 |
| 10 | CTTGCTGACTGCTGT (SEQ ID NO: 291) | GCTCCAGGTTGCCAC (SEQ ID NO: 292) | CTCTGACCCCTGAGT (SEQ ID NO: 293) | TGCTGTCTACTGATC (SEQ ID NO: 294) | 6 |

NOTES
A: AG/GU CONSENSUS; B: IDENTICAL SEQUENCE; C: FROM TRANSFECTION/IVT EXPERIMENT; D: FROM TRANSLATION EXPERIMENTS

Figure 10F:
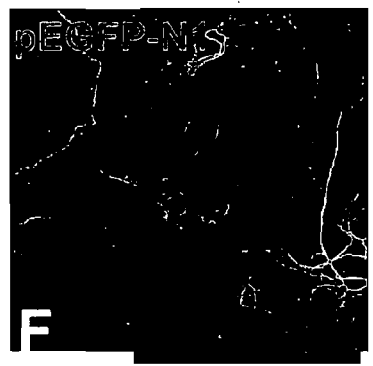
Figure 10G:
Figure 10H:
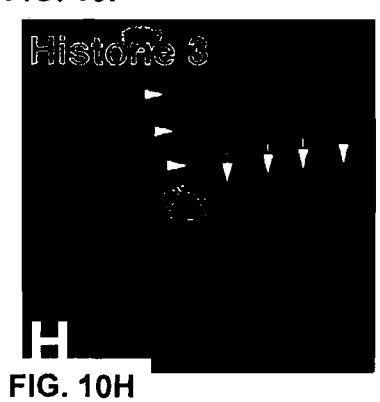
Figure 10I:
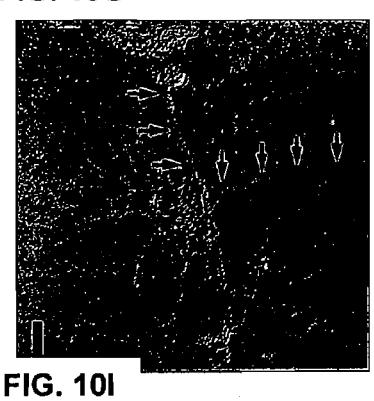
Figure 10J:
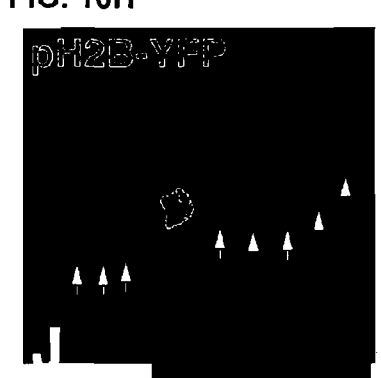
Figure 10K:
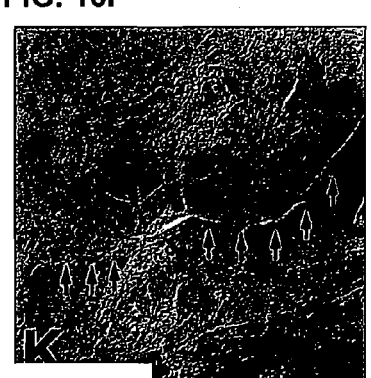

Three additional observations from these experiments are noteworthy. First, when non-neuronal cells from the same cultures are imaged to discern RBP-GFP expression, a distinct staining pattern is routinely observed when compared to neurons that are transfected on the same coverslip. For a majority of the RBP-GFP constructs shown here (with the exception of U2AF65-GFP and Magoh-GFP), subcellular distribution in glia is normally limited to nuclei with extremely modest, if any at all, staining visible in the cytoplasm (see FIG. 10 and FIGS. 2B-2E). Second, when neurons are transfected with the pEGFP-N1 or pDsRed-N1 construct alone, two types of expression are observed; neither of which are seen when we have fused a splice factor RBP in frame with GFP or DsRed. In one instance, GFP is seen distributed throughout the neuronal nuclei and cytoplasm with equal intensity. Often it is not easy to discern a separate nucleus in these GFP-expressing cells. In another instance, the nuclei of neurons and glia have low diffuse levels of GFP staining in nuclei that is offset with distinct cytoplasmic staining and a visible perinuclear ring of expression (FIGS. 10F and 10G). Finally, when we used a well-characterized histone 2B-YFP construct (Platani et al., 2002, Nat. Cell. Biol. 4:502-8) we observed a primarily nuclear pattern of expression (FIG. 10J). These results suggest that specific splicing factors from each of the spliceosome subcomplexes are distributed within the dendritic cytoplasm of neurons, have a variant expression in non-neuronal cells and may be capable of constitutively splicing pre-mRNAs into mature transcripts. Furthermore, experiments conducted with the histone 2B-YFP fusion construct suggests that there is no intrinsic feature of the transfection techniques or the over-expressing GFP fusion constructs that would predispose our experiments to observing a dendritic localization.

Experimental Example 2

Amplification of Spliced CDC RNA from Isolated Dendrites

Given the presence of splicing machinery in dendrites, the potential for RNA splicing to occur in neuronal dendrites was investigated. To perform these experiments, we utilized a pre-RNA splicing construct comprised of exons 14 and 15 of the CDC gene (Ohno et al., 1987, Proc. Natl. Acad. Sci. U.S.A. 84:5187-91) to assess whether it can be spliced in isolated dendrites.

During the time course of these experiments, the viability of isolated dendrites to splice pre-RNA transcripts was assessed. Isolated dendrites have been previously shown to be translationally active (Aakalu et al., 2001, Neuron 30:489-502; Crino et al., 1996, Neuron 17:1173-87; Job et al., 2001, Proc. Natl. Acad. Sci. U.S.A 98:13037-42) with the additional ability to incorporate post-translational sugar precursors of the secreted-protein protein-glycosylation pathway (Torre et al., 1996, J. Neurosci. 16:5967-78). One very sensitive measure of dendritic compromise is mitochondrial function. JC-1, a mitochondrial membrane potential dye (Li et al., 2004, Cell 119:873-87; Arancia et al., 2004, Amino Acids 26:273-82; Ogbourne et al., 2004, Cancer Res. 64:2833-9), was added at varying time point to isolated dendrites. Sequestration of JC-1 by functional mitochondria results in its polymerization and the formation of fluorescent red aggregates (see FIGS. 3 and 10). A comparison of the zero time point and the 5 hr time point show similar levels of red fluorescence. Based on these criteria, these isolated dendrites remain biochemically functional during the time frame of these experiments.

In the CDC pre-RNA the 87 by exon 14 and 73 by exon 15 of the chicken δ-crystalline gene are interrupted by a 257 by intron. The pre-RNA derived from this construct has been used for in vitro pre-RNA splicing assays where spliceosome assembly and CDC pre-RNA splicing were observed (Kataoka et al., 2000, Mol. Cell 6:673-82; Ohno et al., 1987, Proc. Natl. Acad. Sci. U.S.A. 84:5187-91). Briefly, CDC pre-RNA was transcribed from the construct, encoated with the polycationic lipid Metafectene, and manually applied onto dendrites that were isolated from their cognate cell somas as performed previously (Aakalu et al., 2001, Neuron 30:489-502; Crino et al., 1996, Neuron 17:1173-87; Job et al., 2001, Proc. Natl. Acad. Sci. U.S.A 98:13037-42; Kacharmina et al., 2000, Proc. Natl. Acad. Sci. U.S.A. 97:11545-50). After incubation at 37° C. for 30 minutes, RNA was extracted from these isolated dendrites. Reverse transcription of this RNA was primed with an SP6 directed primer inherent to the transfected 3'-end of the CDC RNA construct. The cDNA was then used as template in multiple rounds of PCR using CDC-specific primers with nested primer sets. These PCR amplicons were subcloned and sequenced to determine the splice boundaries utilized in the dendritic subdomain of the neuron.

In addition to a large amount of unspliced CDC pre-RNA, sequence analysis of 53 spliced CDC RNA sequences isolated from eight independent experiments revealed that CDC pre-RNA was spliced using both predicted, consensus and non-canonical splicing sequences (FIG. 1). Four of these sequences adhere to the AG/GU rule for nuclear splicing, while the other sequences make use of cryptic splice sites (Lee et al. 1997, Cancer Res. 57:3131-4). Four other sequences adhere to atypical AT-AC intron splicing, an event requiring the incorporation of SR proteins (Hastings et al., 2001, Rna 7:471-82). Approximately 50% of successful transfection assays resulted in the production of spliced mRNAs suggesting that a subset of dendrites capable of splicing. As with any PCR-dependent protocol, aberrant amplification of unspliced CDC pre-RNA or spliced CDC RNA through mispriming could result in a truncated DNA fragment that would mimic RNA splicing. If these data were the result of such mispriming (internal priming of the CDC cDNA at regions of homology in other CDC cDNAs), then we would expect that a majority of transcripts contain three or more bases of similarity in the donor and acceptor sites at the splice junction (the number of 3'-end primer matched bases to prime PCR) (Wu et al., 1991, DNA Cell Biol. 10:233-8; Liang et al., 1995, Curr. Opin. Immunol. 7:274-80). In contrast, ⅔ of the spliced sequences have two or less bases overlap, suggesting that the PCR reaction was of high fidelity. Furthermore, controls in all experiments showed that PCR amplification of the CDC pre-RNA does not give rise to amplicons distinct from the CDC pre-RNA template.

To show that this splicing event was not unique to the CDC RNA, experiments were repeated using a second, independent construct retaining the SV40 small t-antigen intron. The pGL-2 splicing construct (Promega, Carlsbad, Calif.) contains the luciferase coding region fused to the SV40 small t-antigen intron upstream of the luciferase polyadenylation site. This construct has been used extensively in splicing experiments as a control where it is efficiently spliced in mammalian cells. This luciferase-SV40 sequence was PCR amplified from the pGL-2 plasmid with the 5'-luciferase directed primer containing a T7 RNA polymerase promoter site so that sense RNA can be made from this construct. Following transfection splice product sequences from the luciferase-SV40 chimera were analyzed as described for the CDC pre-RNA splicing experiments using specific primers directed against bases 1680-1700, 1700-1720, 2580-2600, and 2680-2700. Five unique spliced sequences were detected (FIG. 1). As observed with CDC pre-RNA, both conventional and cryptic splice donor/acceptor sites are observed. Cryptic splicing sites with the SV40 small t-antigen intron 3' to some genes has been previously observed (Evans et al., 1989, Gene 84:135-42; Huang et al., 1990, Mol. Cell Biol. 10:1805-10). The characterized sequences are spliced forms some of which show only two bases of 'overlap' as per the pre-CDC splicing discussion above. These data confirm and extend the data from the CDC RNA transfection studies, and further show the RNA splicing capacity of dendrites.

Figure 5A:
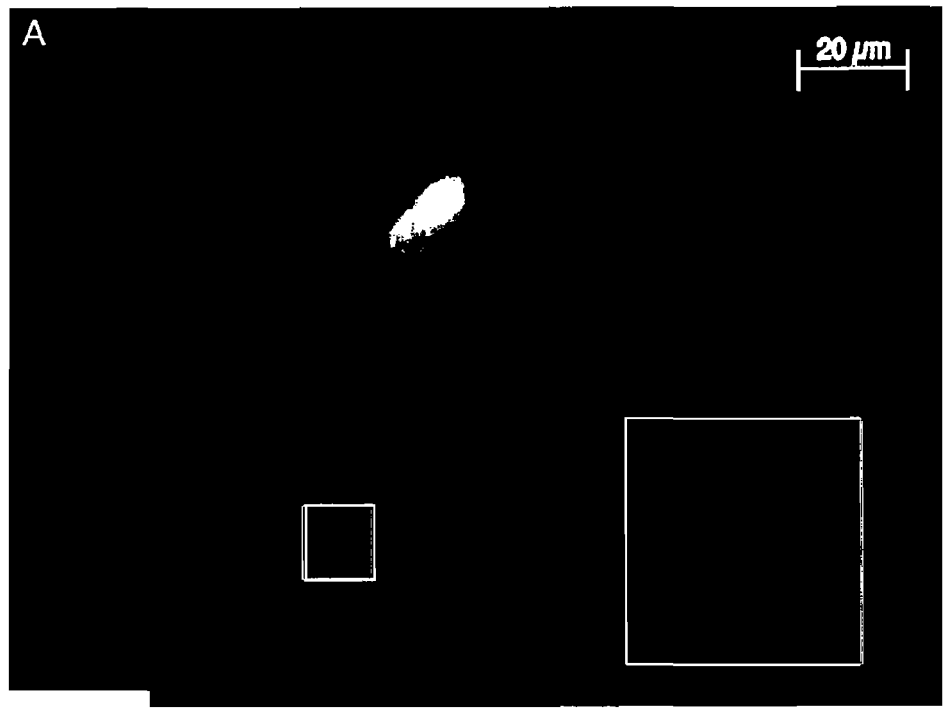
FIG. 5A depicts an inset of an area harvested for detection of spliced products. The yellow appearance of the neuronal nuclei is attributed to blending of the green nuclear fluorescent immunostaining of Sm protein and the red cytoplasmic fluorescent immunostaining of the MAP2 protein.
Figure 5B:
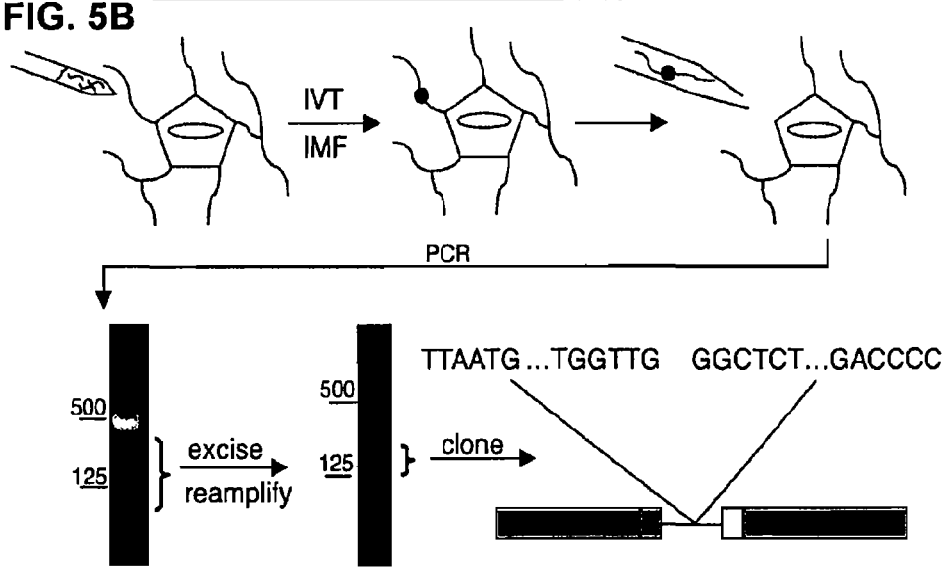
FIG. 5B is a schematic of a methodology for CDC pre-RNA splicing. Briefly, after RNA transfection, in situ transcription (IST) of CDC RNA and immunofluorescence (IMF) detection of Sm granules was performed. Sm proteins positive dendrites were harvested and their nucleic acid components were amplified for spliced CDC RNA content. These PCR amplicons were cloned and sequenced. An intron/exon sequence was derived from the dendrite harvested in FIG. 5A using this methodology.

Amplification of spliced CDC pre-RNA from isolated, Sm antigen-positive dendrites. To conclusively show that a dendrite containing an identified splicing factor can also splice pre-RNA, intact neurons were transfected with CDC pre-RNA, fixed at a later time point with 4% paraformaldehyde, and the dendritically-localized CDC RNA was copied into cDNA using an SP6 primer in situ (FIG. 5A). These dendrites were then immunohistochemically stained for Sm proteins, and a single process containing granule-like structures were harvested. The punctate staining seen in FIG. 5 is qualitatively similar to that seen previously (FIG. 2E). The in situ transcribed cDNA was isolated and used as a PCR template for amplification of spliced CDC RNA. The amplicons of spliced CDC RNA migrates faster than non-spliced CDC pre-RNA during agarose gel electrophores (FIG. 5B) and shows splice donor/acceptor sequence similarity to previous experiments (FIGS. 1 and 5). These data show that Sm antigen-positive processes are capable of supporting dendritic pre-RNA splicing. In experiments where Sm antigen was absent from dendrites, PCR amplification of CDC pre-RNA transfected, Sm-negative, processes yielded no spliced RNAs, suggesting that the inclusion of Sm antigen in dendrites is correlated with the functional splicing activity in dendrites.

Experimental Example 3

Synaptoneurosomes can Splice CDC Pre-RNA

Figure 6:
FIG. 6 is a image depicting a western blot detection of splicing proteins in synaptoneurosomes. Homogenates of whole brain (WB) and synaptoneurosomes (SN) were probed with the corresponding antibody. Numbers on the left depict the relative molecular weight of the protein bands (KDa). The tubulin signal is included at the bottom of the autoradiograms to demonstrate that the same amount of protein was loaded for the whole brain and synaptoneurosome fractions.

Synaptoneurosomes have been used to demonstrate protein synthesis in dendritically enriched regions of neurons (Weiler et al., 1993, Proc. Natl. Acad. Sci. U.S.A. 90:7168-71; Rao et al., 1993, J. Neurochem. 61:835-44; Bagni et al., 2000, J. Neurosci. 20:RC76). This subcellular fraction of tissue homogenates contains liposomes of pre- and post-synaptic entities. Visually, these fractions are absent nuclei (Weiler et al., 1993, Proc. Natl. Acad. Sci. U.S.A. 90:7168-71; Rao et al., 1993, J. Neurochem. 61:835-44; Bagni et al., 2000, J. Neurosci. 20:RC76). Using established protocols, we isolated fresh synaptoneurosomes from rat brain and tested them for the presence of splicing proteins using western blotting. As seen in FIG. 6, U2AF65, pan-SR, SC-35, SF2 and Sm antigens were all present in the whole brain (WB) extract as well as in the synaptoneurosome (SN) preparation. These results show that these same pre-spliceosome proteins, localized in cultured primary dendrites, are present in the WB and, more importantly, the SN fraction at differing abundances. In this respect, the western analysis data is consistent with the immunofluorescence data of FIG. 2. While SN preparations are never purely neuronalin origin, it is unlikely that the observed differing intensities of the protein bands observed with chemiluminscence is function of nuclear contamination as these preparations contain virtually no nuclei and less than 5% mitochondria (Booth et al., 1978, Biochem. J. 176:365-70). Tubulin was used as a loading control to show that the same amount of protein was loaded in the different lanes.

Given the presence of these proteins in SNs, the SN extracts were tested for the ability to splice the CDC pre-RNA. Freshly prepared SNs were supplemented with 1.5 mM ATP and incubated with CDC pre-RNA for 30 minutes at 37° C. After incubation, RNA was isolated from the SNs and the spliced CDC RNA was PCR amplified, cloned and sequenced. Ten spliced sequences generated from three separate experiments are shown in FIG. 1. Consistent with the ATP-dependent nature of the spliceosome and the relative absence of mitochondria in these fractions, no splice forms were generated when ATP was omitted from the SN preparation. A similar effect was observed when SNs were subjected to a single freeze/thaw cycle prior to the splicing assay.

Experimental Example 4

Spliced CDC RNA can be Translated in Isolated Dendrites

Figure 7G:
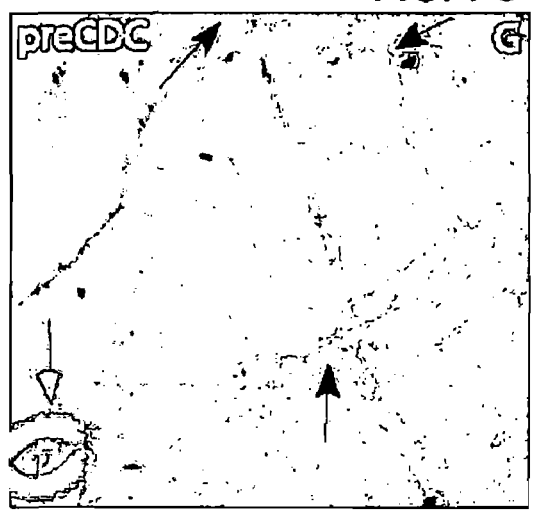
FIGS. 7A, 7D, and 7G depict phase contrast images of whole neurons before cell body removal. Corresponding phase contrast images of isolated dendrites transfected with; no RNA (FIG. 7B), mature CDC RNA (FIG. 7E), or unspliced, CDC pre-RNA (FIG. 7H), and subsequent immunodetection of protein translation with antibody for FLAG and DAB visualization are shown in FIGS. 7C, 7F, and 7I, respectively. Black arrows indicate isolated, transfected dendrites before and after immunodetection of FLAG protein translation. White arrows point out areas previously occupied by cell bodies before dissection.
Figure 7H:
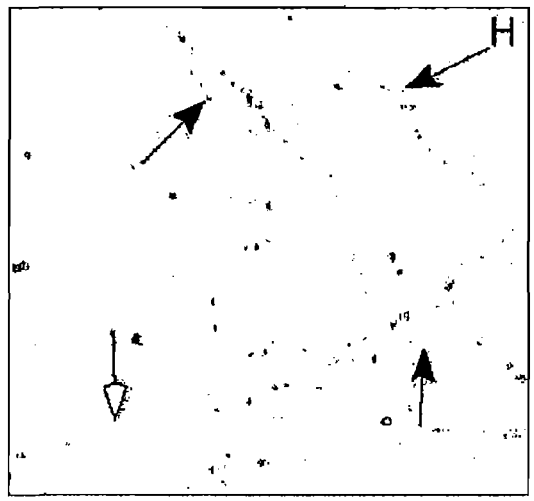
FIG. 7, comprising FIGS. 7A through 7B, demonstrates protein translation from FLAG-tagged CDC pre-mRNA substrate in isolated dendrites.
Figure 7I:
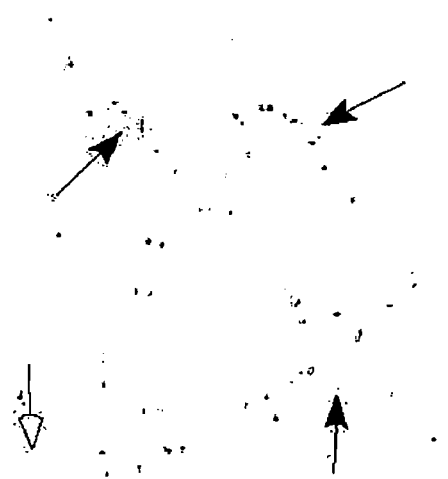

As described previously, the isolated dendrite assay involves mechanical severing of the dendrites from the cell soma, removal of the soma, and transfection of the isolated dendrites. FIGS. 7A, 7D and 7G show photomicrographs of primary rat hippocampal neurons with the cell somas intact (white arrows). FIGS. 7B, 7E and 7H show these same microscopic fields after removal of the soma, leaving the dendrites (black arrows). Since the CDC pre-RNA contains an in-frame FLAG epitope-tag in the second exon this epitope should be immunohistochemically detectable if the dendritically spliced CDC pre-RNA can be translated. Unspliced CDC pre-RNA will not produce a translated FLAG epitope. These same dendrites are stained for FLAG expression after mock transfection (Panel C) and transfection with mature CDC RNA (PanelF) or unspliced CDC pre-RNA (Panel I). These data show the similarity in FLAG sequence expression levels in dendrites when transfected with mature CDC RNA and CDC pre-RNA.

Dendritic transfection of CDC pre-RNA can result in the isolation of alternatively spliced CDCRNAs that contain two adjacent open reading frames (ORFs), with the 3' ORF containing the FLAG epitope (FIG. 1). Therefore, as a result of splicing, bicistronic mRNAs were created from the CDC pre-RNA. To assess whether the FLAG-tags on downstream ORFs are translatable, the 236 by (splice variant 1), 181 by (splice variant 6), and 146 by (splice variant 45) cDNAs were selected and transcribed into RNA that was then transfected into the isolated dendrites, followed by immunostaining with the anti-FLAG antibody. The sequence of the 236 bp, 181 bp, and 146 by cDNAs suggests that if the consensus splice site is not utilized, the sequence extension of the 3'-end of the first exon will give rise to an in-frame termination codon producing a small translational unit. This 5' translational unit does not contain the FLAG-tag. The 236 and 181 by clones both contain a second open reading frame that, if translated, would contain the FLAG-tag. The 146 base sequence is spliced so that there is no in-frame initiator methionine that could prime the expression of the FLAG-tag. FIG. 8 shows that upon in vivo translation, both the 236 by and 181 by alternatively spliced CDC RNAs gave rise to FLAG antigenicity (FIGS. 8A-8B and 8C-8D, respectively). Transfection of the 146 by RNA did not produce FLAG containing protein (FIGS. 8E and 8F). These data indicate that 1) the in-frame methionine for the predicted second open-reading frame produced by nontraditional splicing of the CDC pre-RNA can be recognized by the dendritic protein synthesis machinery and utilized as an initiator methionine to produce protein from the second open-reading frame and 2) these transfected spliced RNAs can be further spliced in the dendrite to yield a mature CDC RNA. The translation of the second open-reading frame of a bicistronic mRNA could occur by read-through of the second reading frame as the ribosomes that translated the first open-reading frame move along the RNA after termination of translation of the first open-reading frame (Kozaket et al., 1998, Nucleic Acids Res. 26:4853-9). Alternatively, translation could occur through utilization of an internal ribosome entry site (IRES) that may be present in the inter-cistronic region in a cap-independent process (Macejak et al., 1991, Nature 353:90-4). M-fold analysis of the spliced CDC RNAs reveals stem-loops and complex secondary structures that have been implicated as potential IRES sites (Martinez-Salas et al., 2002, Biochimie 84:755-63). Regardless of translational mechanism, these data show that dendritically spliced RNAs can be translated in the local dendritic environment.

Experimental Example 5

Control Data for GFP Fusion Constructs

Control experiments were conducted using the Olympus Fluoview FV1000 spectrometer to illustrate the specificity of the GFP fusion constructs used in FIG. 4. As noted elsewhere herein, the intensity of the laser was increased to facilitate imaging of dendritic fluorescence. The fluorescence of the nuclei in these experiments was saturated. In FIG. 10A, a representative image of the "speckled" nuclear pattern of expression is shown using the UAP56-GFP construct. Similar patterns of signal were observed for all GFP fusion proteins exemplified herein. The images set forth in FIG. 10 have been optimized for nuclear images so the intensity of the laser is very low with no increase in gain. A ghosting of GFP expression is visible in the perinuclear region and if the intensity of the laser was increased dendritic staining would be visible as well. In FIGS. 10B-10E are illustrated the two types of non-neuronal staining that observed with GFP fusion constructs set forth in detail elsewhere herein. In the first example, here exemplified by SF1/mBBP-GFP (FIG. 10B) and its corresponding MAP2 immunofluorescence (FIG. 10C), expression is strongly localized to the nucleus with very low levels of cytoplasmic signal. This type of staining pattern was observed for UAP56-GFP and Y14-GFP as well. A second non-neuronal RBP-GFP phenotype is visualized in FIG. 10D with the U2AF65-GFP construct, in which can be observed a well-defined expression in the nucleus with low, but significant fluorescence visible throughout the glial cytoplasm. A similar staining pattern is observed for Magoh-GFP in the glial cell of these cultures (see also FIG. 4A). In FIG. 10E, a transfected neuron (note the MAP2 fluorescence) is also visible in the lower left quadrant of the image. The intensity of staining is apparent in the neuron versus the glia. This difference in RBP-GFP expression was typical when comparing basal levels of expression in neurons and glia. Finally, the expression of the plain pEGFP-N1 construct is illustrated when expressed in glia (FIG. 10F) or neurons (FIG. 10G). There is an obvious difference in the patterns for non-neuronal cells when comparing FIG. 10F to FIGS. 10B and 10D. Similarly, when GFP expression in neurons is not fused to a RBP as described in the present disclosure, there are not distinct patterns of expression. GFP is seen diffusely spread over the nucleus and cytoplasm. This is in contrast to the patterns of expression seen in FIGS. 2 and 4 illustrating the localization of the native protein or the expression of a GFP fusion protein. Finally, in FIGS. 10E-10H are shown control experiments with antigens that should retain a predominantly nuclear localization. An anti-histone 3 antibody (E) and a histone 2B-YFP fusion construct (G) were used to show the respective neuronal localization. Corresponding phase-contrast photos (FIGS. 10F and 10H) illustrate the neuronal morphology. These data show that the use of overexpressing GFP or YFP constructs do not, in all circumstances, lead to localization in the dendritic fields. The arrows in FIGS. 10E and 10F show where the dendrites are localized in the images, while the arrows in FIG. 10G and 10H show the dendrites in this image.

Experimental Example 6

Isolated Dendrite Viability Evaluation Using Mitochondrial Function Measurement Dendrites were isolated from cortical cell cultures and at various times after severing, JC-1 dye (Molecular Probes) was added at a concentration of 1 µg dye/ml media. The dye was incubated at 37° C. with the cultures for 10 min followed by imaging with fluorescence microscopy. Functional mitochondria take up and concentrate the green fluorescent monomer. Once the concentration reached a threshold, the dye began to polymerize, forming red fluorescent aggregates visualized as red puncta. A comparison of the zero time point and the 5 hour time point show similar levels of red fluorescence (FIG. 11).

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of remodeling a dendrite, said method comprising:

transfecting a dendrite with an RNA comprising at least one intron, wherein said dendrite comprises at least one component of a spliceosome and further wherein said at least one component of a spliceosome is capable of splicing an RNA;

wherein said RNA comprising at least one intron is spliced by said at least one component of a spliceosome;

wherein the at least one component of a spliceosome is selected from the group consisting of Y14, Magoh, RNPS1, SC-35, SF2, U2AF65, Smith antigen, pan-SR antigen, U1 snRNP, U2 snRNP, U4 snRNP, U5 snRNP, and U6 snRNP; and wherein said spliced RNA is translated in said dendrite; and wherein said dendrite is thereby remodeled as a consequence of said translation.

2. A method of remodeling a dendrite interaction, said method comprising:

transfecting a dendrite with an RNA comprising at least one intron, wherein said dendrite comprises at least one component of a spliceosome and further wherein said at least one component of a spliceosome is capable of splicing an RNA;

wherein said RNA comprising at least one intron is spliced by said at least one component of a spliceosome;

wherein the at least one component of the spliceosome is selected from the group consisting of Y14, Magoh, RNPS1, SC-35, SF2, U2AF65, Smith antigen, pan-SR antigen, U1 snRNP, U2 snRNP, U4 snRNP, U5 snRNP, and U6 snRNP; and wherein said spliced RNA is translated in said dendrite; and wherein said dendrite interaction is thereby remodeled as a consequence of said translation.

3. A method of remodeling a synaptic network comprising interaction with at least one dendrite, said method comprising:
- transfecting a dendrite with an RNA comprising at least one intron, wherein said dendrite comprises at least one component of a spliceosome and further wherein said at least one component of a spliceosome is capable of splicing an RNA;
- wherein said RNA comprising at least one intron is spliced by said at least one component of a spliceosome;
- wherein the at least one component of the spliceosome is selected from the group consisting of Y14, Magoh, RNPS1, SC-35, SF2, U2AF65, Smith antigen, pan-SR antigen, U1 snRNP, U2 snRNP, U4 snRNP, U5 snRNP, and U6 snRNP; and
- wherein said spliced RNA is translated in said dendrite; and wherein said synaptic network is thereby remodeled as a consequence of said translation.

4. A method of splicing an RNA, said method comprising the steps of:
- a. providing an isolated dendrite comprising at least one component of a spliceosome, wherein said at least one component of a spliceosome is capable of splicing an RNA, and wherein the at least one component of a spliceosome is selected from the group consisting of Y14, Magoh, RNPS1, SC-35, SF2, U2AF65, Smith antigen, pan-SR antigen, U1snRNP, U2 snRNP, U4 snRNP, U5 snRNP, and U6 snRNP; and
- b. transfecting said dendrite with an RNA comprising at least one intron; wherein said RNA comprising at least one intron is spliced by said at least one component of a spliceosome.

5. The method of claim 1, wherein said dendrite is a component of a neuron.

6. The method of claim 1, wherein said dendrite is an isolated dendrite.

7. The method of claim 1, wherein said RNA comprising at least one intron further comprises RNA splicing donor/acceptor pairs, and wherein the RNA splicing donor/acceptor pairs are selected from the group consisting of canonical, atypical and cryptic.

8. The method of claim 1, wherein said RNA comprising at least one intron is a pre-RNA.

9. The method of claim 8, wherein said pre-RNA is a pre-mRNA.

10. The method of claim 1, wherein said RNA comprising at least one intron is transcribed from a nucleic acid comprising a construct selected from the group consisting of pEGFP-N1, pDsRed-N1, splicing factor 1/mammalian branch point binding protein-green fluorescent protein (SF1/mBBP-GFP), U2AF65-GFP, a GFP construct, a DsRed construct, and histone 2B-YFP.

11. A method of translating an RNA, said method comprising the steps of:
- a. providing an isolated dendrite comprising at least one component of a spliceosome, wherein said at least one component of a spliceosome is capable of splicing an RNA, and wherein the at least one component of a spliceosome is selected from the group consisting of Y14, Magoh, RNPS1, SC-35, SF2, U2AF65, Smith antigen, pan-SR antigen, U1snRNP, U2 snRNP, U4 snRNP, U5 snRNP, and U6 snRNP; and
- b. transfecting said dendrite with an RNA comprising at least one intron, wherein said RNA is spliced by said at least one component of a spliceosome;
- further wherein said spliced RNA is translated.

12. A method of splicing an RNA, said method comprising the steps of:
- a. providing an isolated synaptoneurosoine comprising at least one component of a spliceosome, wherein said at least one component of a spliceosome is capable of splicing an RNA, and wherein the at least one component of a spliceosome is selected from the group consisting of Y14, Magoh, RNPS1, SC-35, SF2, U2AF65, Smith antigen, pan-SR antigen, U1 snRNP, U2 snRNP, U4 snRNP, U5 snRNP, and U6 snRNP; and
- b, contacting said synaptoneurosome with an RNA comprising at least one intron;
- wherein said RNA comprising at least one intron is spliced by said at least one component of a spliceosome.

13. A method of translating an RNA, said method comprising the steps of:
- a. providing an isolated synaptoneurosome comprising at least one component of a spliceosome, wherein said at least one component of the spliceosome is capable of splicing an RNA, and wherein the at least one component of a spliceosome is selected from the group consisting of Y14, Magoh, RNPS1, SC-35, SF2, U2AF65, Smith antigen, pan-SR antigen, U1 snRNP, U2 snRNP, U4 snRNP, U5 snRNP, and U6 snRNP;
- b. contacting said synaptoneurosome with an RNA comprising at least one intron, wherein said RNA is spliced by said at least one component of a spliceosome; and
- c. contacting said spliced RNA with a composition capable of translating an RNA under conditions suitable for translating an RNA.

* * * * *

```
                              SEQUENCE LISTING

<160> NUMBER OF SEQ ID NOS: 294

<210> SEQ ID NO 1
<211> LENGTH: 39
<212> TYPE: DNA
<213> ORGANISM: Artificial
<220> FEATURE:
<223> OTHER INFORMATION: reIF4A3 sense primer; chemically synthesized

<400> SEQUENCE: 1
aatgaattcg ccaccatggc ggctaacgcc acgatggcg                              39

<210> SEQ ID NO 2
<211> LENGTH: 36
<212> TYPE: DNA
<213> ORGANISM: Artificial
<220> FEATURE:
<223> OTHER INFORMATION: reIF4A3 antisense primer; chemically
      synthesized

<400> SEQUENCE: 2
atttggatcc cgaattaggt cagccacatt catggg                                 36

<210> SEQ ID NO 3
<211> LENGTH: 39
<212> TYPE: DNA
<213> ORGANISM: Artificial
<220> FEATURE:
<223> OTHER INFORMATION: rMagoh sense primer; chemically synthesized

<400> SEQUENCE: 3
aataagcttg ccaccatgga gagtgacttt tacctgcgt                              39

<210> SEQ ID NO 4
<211> LENGTH: 36
<212> TYPE: DNA
<213> ORGANISM: Artificial
<220> FEATURE:
<223> OTHER INFORMATION: rMagoh antisense primer; chemically synthesized

<400> SEQUENCE: 4
attgaccggt gggattggtt taatcttgaa gtgtaa                                 36

<210> SEQ ID NO 5
<211> LENGTH: 39
<212> TYPE: DNA
<213> ORGANISM: Artificial
<220> FEATURE:
<223> OTHER INFORMATION: rRNPS1 sense primer; chemically synthesized

<400> SEQUENCE: 5
```

-continued

```
aataagcttg ccaccatgga tttatcagga gtgaaaaag                              39

<210> SEQ ID NO 6
<211> LENGTH: 33
<212> TYPE: DNA
<213> ORGANISM: Artificial
<220> FEATURE:
<223> OTHER INFORMATION: rRNPS1 antisense primer; chemically synthesized

<400> SEQUENCE: 6
attgaccggt gggagcagcc gtgaaccaac agt                                    33

<210> SEQ ID NO 7
<211> LENGTH: 39
<212> TYPE: DNA
<213> ORGANISM: Artificial
<220> FEATURE:
<223> OTHER INFORMATION: rSF1/mBBP sense primer; chemically synthesized

<400> SEQUENCE: 7
aatgctagcg ccaccatggc gaccggagcg aacgccacg                              39

<210> SEQ ID NO 8
<211> LENGTH: 33
<212> TYPE: DNA
<213> ORGANISM: Artificial
<220> FEATURE:
<223> OTHER INFORMATION: rSF1/mBBP antisense primer; chemically
      synthesized

<400> SEQUENCE: 8
atttggatcc caatgggcgc ggaaagtcct cac                                    33

<210> SEQ ID NO 9
<211> LENGTH: 39
<212> TYPE: DNA
<213> ORGANISM: Artificial
<220> FEATURE:
<223> OTHER INFORMATION: rU2AF65 sense primer; chemically synthesized

<400> SEQUENCE: 9
aataagcttg ccaccatgga cttcttcaac gcccagatg                              39

<210> SEQ ID NO 10
<211> LENGTH: 33
<212> TYPE: DNA
<213> ORGANISM: Artificial
<220> FEATURE:
<223> OTHER INFORMATION: rU2AF65 antisense primer; chemically
      synthesized

<400> SEQUENCE: 10
atttggatcc cagaagtccc gacggtggta cga                                    33

<210> SEQ ID NO 11
<211> LENGTH: 39
<212> TYPE: DNA
<213> ORGANISM: Artificial
<220> FEATURE:
<223> OTHER INFORMATION: rUAP56 sense primer; chemically synthesized

<400> SEQUENCE: 11
aataagcttg ccaccatggc agagaacgat gtggacaat                              39

<210> SEQ ID NO 12
<211> LENGTH: 33
<212> TYPE: DNA
```

-continued

<213> ORGANISM: Artificial
<220> FEATURE:
<223> OTHER INFORMATION: rUAP56 antisense primer; chemically synthesized

<400> SEQUENCE: 12
atttggatcc cgtgtctgtt caatgtagga gga                            33

<210> SEQ ID NO 13
<211> LENGTH: 39
<212> TYPE: DNA
<213> ORGANISM: Artificial
<220> FEATURE:
<223> OTHER INFORMATION: rY14 sense primer; chemically synthesized

<400> SEQUENCE: 13
aataagcttg ccaccatggc ggacgtgctg gatcttcac                      39

<210> SEQ ID NO 14
<211> LENGTH: 36
<212> TYPE: DNA
<213> ORGANISM: Artificial
<220> FEATURE:
<223> OTHER INFORMATION: rY14 antisense primer; chemically synthesized

<400> SEQUENCE: 14
atttggatcc cgacggcgtc tccggtctgg actcct                         36

<210> SEQ ID NO 15
<211> LENGTH: 19
<212> TYPE: DNA
<213> ORGANISM: Artificial
<220> FEATURE:
<223> OTHER INFORMATION: Sp6 primer; chemically synthesized

<400> SEQUENCE: 15
atttaggtga cactataga                                            19

<210> SEQ ID NO 16
<211> LENGTH: 19
<212> TYPE: DNA
<213> ORGANISM: Artificial
<220> FEATURE:
<223> OTHER INFORMATION: FLAG primer; chemically synthesized

<400> SEQUENCE: 16
tttatcgtca tcgtctttg                                            19

<210> SEQ ID NO 17
<211> LENGTH: 19
<212> TYPE: DNA
<213> ORGANISM: Artificial
<220> FEATURE:
<223> OTHER INFORMATION: 5A primer; chemically synthesized

<400> SEQUENCE: 17
ccaatcgata tacttagcc                                            19

<210> SEQ ID NO 18
<211> LENGTH: 21
<212> TYPE: DNA
<213> ORGANISM: Artificial
<220> FEATURE:
<223> OTHER INFORMATION: 5B primer; chemically synthesized

<400> SEQUENCE: 18
gccagtgcca agcttgctga c                                         21

```
<210> SEQ ID NO 19
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 19
ttaagtgttg tacag                                                     15

<210> SEQ ID NO 20
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 20
atacgagagc tctag                                                     15

<210> SEQ ID NO 21
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 21
ctttgagaca ctaac                                                     15

<210> SEQ ID NO 22
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 22
gtgtccccag ggagc                                                     15

<210> SEQ ID NO 23
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 23
tctcattatt taatg                                                     15

<210> SEQ ID NO 24
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 24
tggttggagg acaca                                                     15

<210> SEQ ID NO 25
<211> LENGTH: 15
<212> TYPE: DNA
<213> ORGANISM: Artificial
<220> FEATURE:
<223> OTHER INFORMATION: sequence fragment of CDC RNA splice product
```

-continued

```
<400> SEQUENCE: 25
catggagaag gctct                                                      15

<210> SEQ ID NO 26
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 26
gacccctgag ttgct                                                      15

<210> SEQ ID NO 27
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 27
ctgtgctcca ggttg                                                      15

<210> SEQ ID NO 28
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 28
ccactggagt gattt                                                      15

<210> SEQ ID NO 29
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 29
aggagaacat ggaga                                                      15

<210> SEQ ID NO 30
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 30
aggctctgac ccctg                                                      15

<210> SEQ ID NO 31
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 31
tgccactgga gtgat                                                      15

<210> SEQ ID NO 32
<211> LENGTH: 15
<212> TYPE: DNA
```

-continued

```
<213> ORGANISM: Artificial
<220> FEATURE:
<223> OTHER INFORMATION: sequence fragment of CDC RNA splice product

<400> SEQUENCE: 32
ttctaccctc caggt                                                  15

<210> SEQ ID NO 33
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 33
catggagaag gctct                                                  15

<210> SEQ ID NO 34
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 34
gacccctgag ttgct                                                  15

<210> SEQ ID NO 35
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 35
aaggtttcag cttct                                                  15

<210> SEQ ID NO 36
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 36
cattatttaa tgtgg                                                  15

<210> SEQ ID NO 37
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 37
tccttttgca ggtca                                                  15

<210> SEQ ID NO 38
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 38
acaaggagaa catgg                                                  15
```

-continued

```
<210> SEQ ID NO 39
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 39
cgagagctct agtct                                                    15

<210> SEQ ID NO 40
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 40
ggtcctaaca tgaag                                                    15

<210> SEQ ID NO 41
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 41
tgcaggtcaa caagg                                                    15

<210> SEQ ID NO 42
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 42
agaacatgga gaagg                                                    15

<210> SEQ ID NO 43
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 43
cattatttaa tgtgg                                                    15

<210> SEQ ID NO 44
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 44
ttggaggaca cattt                                                    15

<210> SEQ ID NO 45
<211> LENGTH: 15
<212> TYPE: DNA
<213> ORGANISM: Artificial
<220> FEATURE:
<223> OTHER INFORMATION: sequence fragment of CDC RNA splice product
```

```
<400> SEQUENCE: 45
ctgcctctcc tcttt                                                        15

<210> SEQ ID NO 46
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 46
gcaggtcaac aagga                                                        15

<210> SEQ ID NO 47
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 47
ttgcgtgttg tacag                                                        15

<210> SEQ ID NO 48
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 48
atacgagagc tctag                                                        15

<210> SEQ ID NO 49
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 49
ctttgagaca ctaac                                                        15

<210> SEQ ID NO 50
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 50
gtgtccccag ggagc                                                        15

<210> SEQ ID NO 51
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 51
ctggagtgat ttcta                                                        15

<210> SEQ ID NO 52
<211> LENGTH: 15
<212> TYPE: DNA
```

```
<213> ORGANISM: Artificial
<220> FEATURE:
<223> OTHER INFORMATION: sequence fragment of CDC RNA splice product

<400> SEQUENCE: 52
ccctccaggt aaggt                                                  15

<210> SEQ ID NO 53
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 53
ctctctctct gcctc                                                  15

<210> SEQ ID NO 54
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 54
tcctctttgc aggtc                                                  15

<210> SEQ ID NO 55
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 55
tttctaccct ccagg                                                  15

<210> SEQ ID NO 56
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 56
taaggtttca gcttc                                                  15

<210> SEQ ID NO 57
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 57
ctctttgcag gtcaa                                                  15

<210> SEQ ID NO 58
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 58
caaggagaac atgga                                                  15
```

-continued

```
<210> SEQ ID NO 59
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 59
tctggtccta acatg                                                    15

<210> SEQ ID NO 60
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 60
ctgacccctc actcc                                                    15

<210> SEQ ID NO 61
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 61
aacatggaga aggct                                                    15

<210> SEQ ID NO 62
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 62
ctgacccctg agttg                                                    15

<210> SEQ ID NO 63
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 63
ccactggagt gattt                                                    15

<210> SEQ ID NO 64
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 64
ctaccctcca ggtaa                                                    15

<210> SEQ ID NO 65
<211> LENGTH: 15
<212> TYPE: DNA
<213> ORGANISM: Artificial
<220> FEATURE:
<223> OTHER INFORMATION: sequence fragment of CDC RNA splice product
```

```
<400> SEQUENCE: 65
ctttgcaggt caaca                                                    15

<210> SEQ ID NO 66
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 66
aggagaacat ggaga                                                    15

<210> SEQ ID NO 67
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 67
acctgctgac tgctg                                                    15

<210> SEQ ID NO 68
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 68
tgctccaggt tgcca                                                    15

<210> SEQ ID NO 69
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 69
caaggagaac atgga                                                    15

<210> SEQ ID NO 70
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 70
gaaggctctg acccc                                                    15

<210> SEQ ID NO 71
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 71
atgtggttgg aggac                                                    15

<210> SEQ ID NO 72
<211> LENGTH: 15
<212> TYPE: DNA
```

```
<213> ORGANISM: Artificial
<220> FEATURE:
<223> OTHER INFORMATION: sequence fragment of CDC RNA splice product

<400> SEQUENCE: 72
cattttaagt gttgt                                                15

<210> SEQ ID NO 73
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 73
ctcctctttg caggt                                                15

<210> SEQ ID NO 74
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 74
caacaaggag aacat                                                15

<210> SEQ ID NO 75
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 75
aggttgccac tggag                                                15

<210> SEQ ID NO 76
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 76
tgatttctac cctcc                                                15

<210> SEQ ID NO 77
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 77
gcctctcctc tttgc                                                15

<210> SEQ ID NO 78
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 78
aggtcaacaa ggaga                                                15
```

<210> SEQ ID NO 79
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 79
gtttcagctt ctcat                                                    15

<210> SEQ ID NO 80
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 80
tatttaatgt ggttg                                                    15

<210> SEQ ID NO 81
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 81
atggagaagg ctctg                                                    15

<210> SEQ ID NO 82
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 82
acccctgagt tgctg                                                    15

<210> SEQ ID NO 83
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 83
ctctagtctg gtcct                                                    15

<210> SEQ ID NO 84
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 84
aacatgaaga cttgc                                                    15

<210> SEQ ID NO 85
<211> LENGTH: 15
<212> TYPE: DNA
<213> ORGANISM: Artificial
<220> FEATURE:
<223> OTHER INFORMATION: sequence fragment of CDC RNA splice product -continued

```
<400> SEQUENCE: 85
aacaaggaga acatg                                                     15

<210> SEQ ID NO 86
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 86
gagaaggctc tgacc                                                     15

<210> SEQ ID NO 87
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 87
ctgtgctcca ggttg                                                     15

<210> SEQ ID NO 88
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 88
ccactggagt gattt                                                     15

<210> SEQ ID NO 89
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 89
caaggagaac atgga                                                     15

<210> SEQ ID NO 90
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 90
gaaggctctg acccc                                                     15

<210> SEQ ID NO 91
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 91
ctcattattt aatgt                                                     15

<210> SEQ ID NO 92
<211> LENGTH: 15
<212> TYPE: DNA
```

```
<213> ORGANISM: Artificial
<220> FEATURE:
<223> OTHER INFORMATION: sequence fragment of CDC RNA splice product

<400> SEQUENCE: 92
ggttggagga cacat                                                         15

<210> SEQ ID NO 93
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 93
agaaggctct gaccc                                                         15

<210> SEQ ID NO 94
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 94
ctgagttgct gtcta                                                         15

<210> SEQ ID NO 95
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 95
cttctcatta tttaa                                                         15

<210> SEQ ID NO 96
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 96
tgtggttgga ggaca                                                         15

<210> SEQ ID NO 97
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 97
ggagaaggct ctgac                                                         15

<210> SEQ ID NO 98
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 98
ccctgagttg ctgtc                                                         15
```

```
<210> SEQ ID NO 99
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 99
agtaaggttt cagct                                                      15

<210> SEQ ID NO 100
<211> LENGTH: 16
<212> TYPE: DNA
<213> ORGANISM: Artificial
<220> FEATURE:
<223> OTHER INFORMATION: sequence fragment of CDC RNA splice product

<400> SEQUENCE: 100
tctcattatt taatgt                                                     16

<210> SEQ ID NO 101
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 101
gttgtgtcta ctgat                                                      15

<210> SEQ ID NO 102
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 102
cggggtagac tacaa                                                      15

<210> SEQ ID NO 103
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 103
gactgctgtg ctcca                                                      15

<210> SEQ ID NO 104
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 104
ggttgccact ggagt                                                      15

<210> SEQ ID NO 105
<211> LENGTH: 15
<212> TYPE: DNA
<213> ORGANISM: Artificial
<220> FEATURE:
<223> OTHER INFORMATION: sequence fragment of CDC RNA splice product
```

```
<400> SEQUENCE: 105
ctctttgcag gtcaa                                                         15

<210> SEQ ID NO 106
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 106
caaggagaac atgga                                                         15

<210> SEQ ID NO 107
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 107
tggagtgatt tctac                                                         15

<210> SEQ ID NO 108
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 108
cctccaggta aggtt                                                         15

<210> SEQ ID NO 109
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 109
gcaaatgata acctc                                                         15

<210> SEQ ID NO 110
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 110
tctctctgcc tctcc                                                         15

<210> SEQ ID NO 111
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 111
tagtctggtc ctaac                                                         15

<210> SEQ ID NO 112
<211> LENGTH: 15
<212> TYPE: DNA
```

```
<213> ORGANISM: Artificial
<220> FEATURE:
<223> OTHER INFORMATION: sequence fragment of CDC RNA splice product

<400> SEQUENCE: 112
atgaagactt gctca                                                      15

<210> SEQ ID NO 113
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 113
gagaaggctc tgacc                                                      15

<210> SEQ ID NO 114
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 114
cctgagttgc tgtct                                                      15

<210> SEQ ID NO 115
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 115
catgaagact tgctc                                                      15

<210> SEQ ID NO 116
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 116
actcctactg cttgt                                                      15

<210> SEQ ID NO 117
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 117
ggagaaggct ctgac                                                      15

<210> SEQ ID NO 118
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 118
ccctgagttg ctgtc                                                      15
```

```
<210> SEQ ID NO 119
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 119
ggacacattt taagt                                                      15

<210> SEQ ID NO 120
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 120
gttgtacaga tacga                                                      15

<210> SEQ ID NO 121
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 121
tctctctctg cctct                                                      15

<210> SEQ ID NO 122
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 122
cctctttgca ggtca                                                      15

<210> SEQ ID NO 123
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 123
gagtgatttc taccc                                                      15

<210> SEQ ID NO 124
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 124
tccaggtaag gtttc                                                      15

<210> SEQ ID NO 125
<211> LENGTH: 15
<212> TYPE: DNA
<213> ORGANISM: Artificial
<220> FEATURE:
<223> OTHER INFORMATION: sequence fragment of CDC RNA splice product
```

```
<400> SEQUENCE: 125
ggagaaggct ctgac                                                          15

<210> SEQ ID NO 126
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 126
ccctgagttg ctgtc                                                          15

<210> SEQ ID NO 127
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 127
aggacacatt ttaag                                                          15

<210> SEQ ID NO 128
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 128
tgttgtacag atacg                                                          15

<210> SEQ ID NO 129
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 129
aggctctgac ccctg                                                          15

<210> SEQ ID NO 130
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 130
agttgctgtc tactg                                                          15

<210> SEQ ID NO 131
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 131
tgctgtgctc caggt                                                          15

<210> SEQ ID NO 132
<211> LENGTH: 15
<212> TYPE: DNA
```

```
<213> ORGANISM: Artificial
<220> FEATURE:
<223> OTHER INFORMATION: sequence fragment of CDC RNA splice product

<400> SEQUENCE: 132
tgccactgga gtgat                                                         15

<210> SEQ ID NO 133
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 133
gacccctgag ttgct                                                         15

<210> SEQ ID NO 134
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 134
gtctactgat cgggt                                                         15

<210> SEQ ID NO 135
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 135
gagtgatttc taccc                                                         15

<210> SEQ ID NO 136
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 136
ccctgtaagg tttca                                                         15

<210> SEQ ID NO 137
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 137
agaaggctct gaccc                                                         15

<210> SEQ ID NO 138
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 138
ccctgagttg ctgtc                                                         15
```

```
<210> SEQ ID NO 139
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 139
gttgtacaga tacga                                                     15

<210> SEQ ID NO 140
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 140
gctctagtct ggtcc                                                     15

<210> SEQ ID NO 141
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 141
aggagaacat ggaga                                                     15

<210> SEQ ID NO 142
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 142
aggctctgac ccctg                                                     15

<210> SEQ ID NO 143
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 143
agtaaggttt cagct                                                     15

<210> SEQ ID NO 144
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 144
tctcattatt taatg                                                     15

<210> SEQ ID NO 145
<211> LENGTH: 15
<212> TYPE: DNA
<213> ORGANISM: Artificial
<220> FEATURE:
<223> OTHER INFORMATION: sequence fragment of CDC RNA splice product
```

```
<400> SEQUENCE: 145
caaatgataa cctct                                                    15

<210> SEQ ID NO 146
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 146
ctctctgcct ctcct                                                    15

<210> SEQ ID NO 147
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 147
aggtaaggtt tcagc                                                    15

<210> SEQ ID NO 148
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 148
ctctcctctt tgcag                                                    15

<210> SEQ ID NO 149
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 149
aacctctctc tctgc                                                    15

<210> SEQ ID NO 150
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 150
ctctcctctt tgcag                                                    15

<210> SEQ ID NO 151
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 151
tgactgctgt gctcc                                                    15

<210> SEQ ID NO 152
<211> LENGTH: 15
<212> TYPE: DNA
```

```
<213> ORGANISM: Artificial
<220> FEATURE:
<223> OTHER INFORMATION: sequence fragment of CDC RNA splice product

<400> SEQUENCE: 152
caggttgcca ctgga                                                    15

<210> SEQ ID NO 153
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 153
gagaaggctc tgacc                                                    15

<210> SEQ ID NO 154
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 154
cctgagttgc tgtct                                                    15

<210> SEQ ID NO 155
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 155
tttctaccct ccagg                                                    15

<210> SEQ ID NO 156
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 156
taaggtttca gcttc                                                    15

<210> SEQ ID NO 157
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 157
agaacatgga gaagg                                                    15

<210> SEQ ID NO 158
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 158
ctctgacccc tgagt                                                    15
```

```
<210> SEQ ID NO 159
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 159
tgctgtgctc caggt                                                    15

<210> SEQ ID NO 160
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 160
gccactggag tgatt                                                    15

<210> SEQ ID NO 161
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 161
gtctactgat cgggt                                                    15

<210> SEQ ID NO 162
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 162
agactacaaa gacga                                                    15

<210> SEQ ID NO 163
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 163
gatttctacc cccca                                                    15

<210> SEQ ID NO 164
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 164
tgtaaggttt cagct                                                    15

<210> SEQ ID NO 165
<211> LENGTH: 15
<212> TYPE: DNA
<213> ORGANISM: Artificial
<220> FEATURE:
<223> OTHER INFORMATION: sequence fragment of CDC RNA splice product
```

```
<400> SEQUENCE: 165
ccttgatgaa gtcca                                                         15

<210> SEQ ID NO 166
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 166
ttctttgaga cacta                                                         15

<210> SEQ ID NO 167
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 167
ggtttcagct tctca                                                         15

<210> SEQ ID NO 168
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 168
ttatttaatg tggtt                                                         15

<210> SEQ ID NO 169
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 169
cctctttgca ggtca                                                         15

<210> SEQ ID NO 170
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 170
acaaggagaa catgg                                                         15

<210> SEQ ID NO 171
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 171
ctctagtctg gtcct                                                         15

<210> SEQ ID NO 172
<211> LENGTH: 15
<212> TYPE: DNA
```

```
<213> ORGANISM: Artificial
<220> FEATURE:
<223> OTHER INFORMATION: sequence fragment of CDC RNA splice product

<400> SEQUENCE: 172
aacatgaaga cttgc                                                     15

<210> SEQ ID NO 173
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 173
aaggctctga cccct                                                     15

<210> SEQ ID NO 174
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 174
gagttgctgt ctact                                                     15

<210> SEQ ID NO 175
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 175
gctgactgct gtgct                                                     15

<210> SEQ ID NO 176
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 176
ccaggttgcc actgg                                                     15

<210> SEQ ID NO 177
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 177
gacccctgag ttgct                                                     15

<210> SEQ ID NO 178
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 178
gtctactgat cgggt                                                     15
```

```
<210> SEQ ID NO 179
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 179
gtgatttcta ccctc                                                          15

<210> SEQ ID NO 180
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 180
caggtaaggt ttcag                                                          15

<210> SEQ ID NO 181
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 181
ctctctctct gcctc                                                          15

<210> SEQ ID NO 182
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 182
tcctctttgc aggtc                                                          15

<210> SEQ ID NO 183
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 183
tgatttctac cctcc                                                          15

<210> SEQ ID NO 184
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 184
tgtaaggttt cagct                                                          15

<210> SEQ ID NO 185
<211> LENGTH: 15
<212> TYPE: DNA
<213> ORGANISM: Artificial
<220> FEATURE:
<223> OTHER INFORMATION: sequence fragment of CDC RNA splice product
```

```
<400> SEQUENCE: 185
tctctctgcc tctcc                                                    15

<210> SEQ ID NO 186
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 186
tctttgcagg tcaac                                                    15

<210> SEQ ID NO 187
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 187
tatttaatgt ggttg                                                    15

<210> SEQ ID NO 188
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 188
gaggacacat tttaa                                                    15

<210> SEQ ID NO 189
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 189
ctgacccctg agttg                                                    15

<210> SEQ ID NO 190
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 190
ctgtctactg atcgg                                                    15

<210> SEQ ID NO 191
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 191
gtgatttcta ccctc                                                    15

<210> SEQ ID NO 192
<211> LENGTH: 15
<212> TYPE: DNA
```

```
<213> ORGANISM: Artificial
<220> FEATURE:
<223> OTHER INFORMATION: sequence fragment of CDC RNA splice product

<400> SEQUENCE: 192
caggtaaggt ttcag                                                    15

<210> SEQ ID NO 193
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 193
tctctgcctc tcctc                                                    15

<210> SEQ ID NO 194
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 194
tttgcaggtc aacaa                                                    15

<210> SEQ ID NO 195
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 195
ctggtcctaa catga                                                    15

<210> SEQ ID NO 196
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 196
agacttgctc actcc                                                    15

<210> SEQ ID NO 197
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 197
gggagcagca aatga                                                    15

<210> SEQ ID NO 198
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 198
taacctctct ctctg                                                    15
```

```
<210> SEQ ID NO 199
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 199
accctccagg taagg                                                     15

<210> SEQ ID NO 200
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 200
tttcagcttc tcatt                                                     15

<210> SEQ ID NO 201
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 201
tgcaggtcaa caagg                                                     15

<210> SEQ ID NO 202
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 202
agaacatgga gaagg                                                     15

<210> SEQ ID NO 203
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 203
tttaatgtga agact                                                     15

<210> SEQ ID NO 204
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 204
tgctcactcc tactg                                                     15

<210> SEQ ID NO 205
<211> LENGTH: 15
<212> TYPE: DNA
<213> ORGANISM: Artificial
<220> FEATURE:
<223> OTHER INFORMATION: sequence fragment of CDC RNA splice product
```

```
<400> SEQUENCE: 205
ctgatcgggt agact                                                      15

<210> SEQ ID NO 206
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 206
acaaagacga tgacg                                                      15

<210> SEQ ID NO 207
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 207
tgctgtgctc caggt                                                      15

<210> SEQ ID NO 208
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 208
tgccactgga gtgat                                                      15

<210> SEQ ID NO 209
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 209
ctcctctttg caggt                                                      15

<210> SEQ ID NO 210
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 210
caacaaggag aacat                                                      15

<210> SEQ ID NO 211
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 211
tctggtccta acatg                                                      15

<210> SEQ ID NO 212
<211> LENGTH: 15
<212> TYPE: DNA
```

```
<213> ORGANISM: Artificial
<220> FEATURE:
<223> OTHER INFORMATION: sequence fragment of CDC RNA splice product

<400> SEQUENCE: 212
aagacttgcg tgttg                                                          15

<210> SEQ ID NO 213
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 213
aacaaggaga acatg                                                          15

<210> SEQ ID NO 214
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 214
gagaaggctc tgacc                                                          15

<210> SEQ ID NO 215
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 215
gtgccaagct tgctg                                                          15

<210> SEQ ID NO 216
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 216
actgctgtgc tccag                                                          15

<210> SEQ ID NO 217
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 217
acccctgagt tgctg                                                          15

<210> SEQ ID NO 218
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 218
tctactgatc gggta                                                          15
```

```
<210> SEQ ID NO 219
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 219
cttgctgact gctgt                                                         15

<210> SEQ ID NO 220
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 220
gctccaggtt gccac                                                         15

<210> SEQ ID NO 221
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 221
cccctgagtt gctgt                                                         15

<210> SEQ ID NO 222
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 222
ctactgatcg ggtag                                                         15

<210> SEQ ID NO 223
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 223
ttgctactcc tactg                                                         15

<210> SEQ ID NO 224
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 224
cttgttatga cccca                                                         15

<210> SEQ ID NO 225
<211> LENGTH: 15
<212> TYPE: DNA
<213> ORGANISM: Artificial
<220> FEATURE:
<223> OTHER INFORMATION: sequence fragment of CDC RNA splice product
```

```
<400> SEQUENCE: 225
agttgctgtc tactg                                                          15

<210> SEQ ID NO 226
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 226
atcgggtaga ctaca                                                          15

<210> SEQ ID NO 227
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 227
tctggtccta acatg                                                          15

<210> SEQ ID NO 228
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 228
aagacttgct cactc                                                          15

<210> SEQ ID NO 229
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 229
aacaaggaga acatg                                                          15

<210> SEQ ID NO 230
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 230
gagaaggctc tgacc                                                          15

<210> SEQ ID NO 231
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 231
tttaatgtga agact                                                          15

<210> SEQ ID NO 232
<211> LENGTH: 15
<212> TYPE: DNA
```

```
<213> ORGANISM: Artificial
<220> FEATURE:
<223> OTHER INFORMATION: sequence fragment of CDC RNA splice product

<400> SEQUENCE: 232
tgctcactcc tactg                                                        15

<210> SEQ ID NO 233
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 233
ctgatcgggt agact                                                        15

<210> SEQ ID NO 234
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 234
acaaagacga tgacg                                                        15

<210> SEQ ID NO 235
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 235
aaagtccaaa ttgta                                                        15

<210> SEQ ID NO 236
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 236
ccaaattgta aaatg                                                        15

<210> SEQ ID NO 237
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 237
tactgttttt tctta                                                        15

<210> SEQ ID NO 238
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 238
ctccacacag gcata                                                        15
```

-continued

```
<210> SEQ ID NO 239
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 239
aagtccaaat tgtaa                                                         15

<210> SEQ ID NO 240
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 240
aatgtaactg tattc                                                         15

<210> SEQ ID NO 241
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 241
cagttataat cataa                                                         15

<210> SEQ ID NO 242
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 242
catactgttt tttct                                                         15

<210> SEQ ID NO 243
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 243
ttacgtcgcc agtca                                                         15

<210> SEQ ID NO 244
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 244
agtaacaacc gcgaa                                                         15

<210> SEQ ID NO 245
<211> LENGTH: 15
<212> TYPE: DNA
<213> ORGANISM: Artificial
<220> FEATURE:
<223> OTHER INFORMATION: sequence fragment of CDC RNA splice product
```

```
<400> SEQUENCE: 245
taacagttat aatca                                                          15

<210> SEQ ID NO 246
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 246
taacatactg ttttt                                                          15

<210> SEQ ID NO 247
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 247
cttaccggaa aactc                                                          15

<210> SEQ ID NO 248
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 248
gacgcaagaa aaatc                                                          15

<210> SEQ ID NO 249
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 249 tgtttttict tactc                                                          15

<210> SEQ ID NO 250
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 250
cacacaggca tagag                                                          15

<210> SEQ ID NO 251
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 251
gatgacggaa aaaga                                                          15

<210> SEQ ID NO 252
<211> LENGTH: 15
<212> TYPE: DNA
```

```
<213> ORGANISM: Artificial
<220> FEATURE:
<223> OTHER INFORMATION: sequence fragment of CDC RNA splice product

<400> SEQUENCE: 252
gatcgtggat tacgt                                                    15

<210> SEQ ID NO 253
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 253
ctcctccaaa aaaga                                                    15

<210> SEQ ID NO 254
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 254
agagaaaggt agaag                                                    15

<210> SEQ ID NO 255
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 255
cttgctcact cctac                                                    15

<210> SEQ ID NO 256
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 256
tgcttgttat gaccc                                                    15

<210> SEQ ID NO 257
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 257
ctactgatcg ggtag                                                    15

<210> SEQ ID NO 258
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 258
actacaaaga cgatg                                                    15
```

```
<210> SEQ ID NO 259
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 259
ttttaagtgt tgtac                                                    15

<210> SEQ ID NO 260
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 260
agatacgaga gctct                                                    15

<210> SEQ ID NO 261
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 261
tctctgcctc tcctc                                                    15

<210> SEQ ID NO 262
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 262
gataacctct ctctc                                                    15

<210> SEQ ID NO 263
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 263
ttcagcttct catta                                                    15

<210> SEQ ID NO 264
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 264
tttaatgtgg ttgga                                                    15

<210> SEQ ID NO 265
<211> LENGTH: 15
<212> TYPE: DNA
<213> ORGANISM: Artificial
<220> FEATURE:
<223> OTHER INFORMATION: sequence fragment of CDC RNA splice product
```

-continued

```
<400> SEQUENCE: 265
tcctctttgc aggtc                                                      15

<210> SEQ ID NO 266
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 266
aacaaggaga acatg                                                      15

<210> SEQ ID NO 267
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 267
aggtttcagc ttctc                                                      15

<210> SEQ ID NO 268
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 268
attatttaat gtggt                                                      15

<210> SEQ ID NO 269
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 269
cctctctctc tgcct                                                      15

<210> SEQ ID NO 270
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 270
ctcctctttg caggt                                                      15

<210> SEQ ID NO 271
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 271
ctgactgctg tgctc                                                      15

<210> SEQ ID NO 272
<211> LENGTH: 15
<212> TYPE: DNA
```

```
<213> ORGANISM: Artificial
<220> FEATURE:
<223> OTHER INFORMATION: sequence fragment of CDC RNA splice product

<400> SEQUENCE: 272
caggttgcca ctgga                                                        15

<210> SEQ ID NO 273
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 273
ccccaccaca ggcag                                                        15

<210> SEQ ID NO 274
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 274
ctcagataca cttgg                                                        15

<210> SEQ ID NO 275
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 275
cctccaggta aggtt                                                        15

<210> SEQ ID NO 276
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 276
tcagcttctc attat                                                        15

<210> SEQ ID NO 277
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 277
tgctgtctac tgatc                                                        15

<210> SEQ ID NO 278
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 278
gggtagacta caaag                                                        15
```

```
<210> SEQ ID NO 279
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 279
aggtttcagc ttctc                                                      15

<210> SEQ ID NO 280
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 280
attatttaat gtggt                                                      15

<210> SEQ ID NO 281
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 281
aaatgataac ctctc                                                      15

<210> SEQ ID NO 282
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 282
tctctgcctc tcctc                                                      15

<210> SEQ ID NO 283
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 283
gcttgttatg acccc                                                      15

<210> SEQ ID NO 284
<211> LENGTH: 16
<212> TYPE: DNA
<213> ORGANISM: Artificial
<220> FEATURE:
<223> OTHER INFORMATION: sequence fragment of CDC RNA splice product

<400> SEQUENCE: 284
accacaggca gctcag                                                     16

<210> SEQ ID NO 285
<211> LENGTH: 15
<212> TYPE: DNA
<213> ORGANISM: Artificial
<220> FEATURE:
<223> OTHER INFORMATION: sequence fragment of CDC RNA splice product
```

```
<400> SEQUENCE: 285
acatggagaa ggctc                                                    15

<210> SEQ ID NO 286
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 286
tgacccctga gttgc                                                    15

<210> SEQ ID NO 287
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 287
ttcagcttct catta                                                    15

<210> SEQ ID NO 288
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 288
tttaatgtgg ttgga                                                    15

<210> SEQ ID NO 289
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 289
cattctttga gacac                                                    15

<210> SEQ ID NO 290
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 290
taacgtgtcc ccagg                                                    15

<210> SEQ ID NO 291
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 291
cttgctgact gctgt                                                    15

<210> SEQ ID NO 292
<211> LENGTH: 15
<212> TYPE: DNA
```

-continued

```
<213> ORGANISM: Artificial
<220> FEATURE:
<223> OTHER INFORMATION: sequence fragment of CDC RNA splice product

<400> SEQUENCE: 292
gctccaggtt gccac                                                          15

<210> SEQ ID NO 293
<211> LENGTH: 15
<212> TYPE: DNA
<213> ORGANISM: Artificial
<220> FEATURE:
<223> OTHER INFORMATION: sequence fragment of CDC RNA splice product

<400> SEQUENCE: 293
ctctgacccc tgagt                                                          15

<210> SEQ ID NO 294
<211> LENGTH: 29
<212> TYPE: DNA
<213> ORGANISM: Artificial
<220> FEATURE:
<223> OTHER INFORMATION: sequence fragment of CDC RNA splice product
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 294
tgctgtctac tgatccntnd cntndnsns                                           29
```